US012734231B2

(12) United States Patent
Breen et al.

(10) Patent No.: US 12,734,231 B2
(45) Date of Patent: Sep. 15, 2026

(54) CELL CULTURE PROCESS FOR PRODUCING RSV F PROTEIN

(71) Applicant: Pfizer Inc., New York, NY (US)

(72) Inventors: Shelby Hutchins Breen, North Andover, MA (US); Cameron Albert Harrington, Somerville, MA (US); Michaela Evelina Jacobs, San Diego, CA (US); Jason Arnold Lotvin, West Nyack, NY (US); Bhanu Chandra Mulukutla, Tewksbury, MA (US); David Stead, Weehawken, NJ (US); Madhuresh Sumit, Andover, MA (US)

(73) Assignee: Pfizer Inc., New York, NY (US)

( * ) Notice: Subject to any disclaimer, the term of this patent is extended or adjusted under 35 U.S.C. 154(b) by 620 days.

(21) Appl. No.: 18/247,565

(22) PCT Filed: Sep. 30, 2021

(86) PCT No.: PCT/IB2021/058995

§ 371 (c)(1),
(2) Date: Mar. 31, 2023

(87) PCT Pub. No.: WO2022/070129

PCT Pub. Date: Apr. 7, 2022

(65) Prior Publication Data

US 2024/0016915 A1 Jan. 18, 2024

Related U.S. Application Data

(60) Provisional application No. 63/086,702, filed on Oct. 2, 2020.

(51) Int. Cl.

| | |
|---|---|
| ***A61K 39/12*** | (2006.01) |
| ***C07K 14/005*** | (2006.01) |
| ***C12N 7/00*** | (2006.01) |
| ***C12N 7/01*** | (2006.01) |
| ***C12P 21/00*** | (2006.01) |

(52) U.S. Cl.

CPC ............ *A61K 39/12* (2013.01); *C07K 14/005* (2013.01); *C12N 7/00* (2013.01); *C12P 21/005* (2013.01); *C12N 2760/18522* (2013.01); *C12N 2760/18534* (2013.01); *C12N 2760/18552* (2013.01)

(58) Field of Classification Search

CPC .................. A61K 39/12; C07K 14/005; C12N 2760/18522; C12N 2760/18552; C12N 7/00

See application file for complete search history.

(56) References Cited

U.S. PATENT DOCUMENTS

| | | | |
|---|---|---|---|
| 4,339,216 | A | 7/1982 | Bell |
| 5,057,540 | A | 10/1991 | Kensil et al. |
| 5,166,320 | A | 11/1992 | Wu et al. |
| 2005/0070013 | A1 | 3/2005 | Luan et al. |

FOREIGN PATENT DOCUMENTS

| | | | |
|---|---|---|---|
| EP | 0117058 | A2 | 8/1984 |
| EP | 0117060 | A2 | 8/1984 |
| WO | 90/03184 | A1 | 4/1990 |
| WO | 90/14837 | A1 | 12/1990 |
| WO | 96/11711 | A1 | 4/1996 |
| WO | 2002/066603 | A2 | 8/2002 |
| WO | 2004/004762 | A1 | 1/2004 |
| WO | 2009/079796 | | 12/2004 |
| WO | 2005/002620 | A1 | 1/2005 |
| WO | 2006/026445 | A1 | 3/2006 |
| WO | 2006/050050 | A2 | 5/2006 |
| WO | 2008/063892 | A2 | 5/2008 |
| WO | 2008/109410 | A1 | 9/2008 |
| WO | 2008/147196 | A2 | 12/2008 |
| WO | 2004/104186 | | 7/2009 |
| WO | 2010/149745 | A1 | 12/2010 |
| WO | 2011/008974 | A2 | 1/2011 |
| WO | 2011/134919 | A2 | 11/2011 |
| WO | 2014/160463 | A1 | 10/2014 |
| WO | 2014/174018 | A1 | 10/2014 |
| WO | 2014/202570 | A1 | 12/2014 |
| WO | 2015/013551 | A1 | 1/2015 |
| WO | 2015/140708 | A1 | 9/2015 |
| WO | 2015/177312 | A1 | 11/2015 |
| WO | 2015/186075 | A1 | 12/2015 |
| WO | 2017/005848 | A1 | 1/2017 |
| WO | 2017/109629 | A1 | 6/2017 |
| WO | 2018/109220 | A2 | 6/2018 |

OTHER PUBLICATIONS

Day, N.D. et al.: "Contribution of cysteine residues in the extracellular domain of the F protein of human respiratory syncytial virus to its function", Virology Journal, vol. 3, No. 1, May 24, 2006, pp. 34-44.
Gagnon, M. et al.: "High-End pH-Controlled Delivery of Glucose Effectively Suppresses Lactate Accumulation in CHO Fed-Batch Cultures", Biotechnology and Bioengineering, vol. 108, No. 6, Feb. 24, 2011, pp. 1328-1337.
Berkner, K.L., "Development of Adenovirus Vectors for the Expression of Heterologous Genes", BioTechniques, 1988, 6(7):616-629.
Chaiwatpongsakorn, S., et al., "Soluble Respiratory Syncytial Virus Fusion Protein in the Fully Cleaved, Pretriggered State Is Triggered by Exposure to Low-Molarity Buffer", Journal of Virology, 2011, 85(8):3968-3977.
Datta, R. et al., "Ionizing radiation activates transcription of the EGRI gene via CArG elements", Proc. Natl. Acad. Sci. USA, 1992, 89:10149-10153.
Dormitzer, P.R., et al., "Structural vaccinology starts to deliver", Nature Reviews Microbiology, 2012, 10(12):807-813.

(Continued)

*Primary Examiner* — Barry A Chestnut

(57) ABSTRACT

The invention relates to methods for producing an RSV F protein trimer in a fed batch cell culture.

25 Claims, 17 Drawing Sheets

Specification includes a Sequence Listing.

(56) References Cited

OTHER PUBLICATIONS

Flotte, T.R., et al., "Expression of the Cystic Fibrosis Transmembrane Conductance Regulator from a Novel Adeno-associated Virus Promoter", The Journal of Biological Chemistry, 1993, 268(5):3781-3790.
Flotte, T.R., et al., "Gene Expression from Adeno-associated Virus Vectors in Airway Epithelial Cells", American Journal of Respiratory Cell and Molecular Biology, 1992, 7(3):349-356.
Furukawa, K. and Ohsuye, K., "Effect of culture temperature on a recombinant CHO cell line producing a C-terminal alpha-amidating enzyme", Cytotechnology, 1998, 26(2):153-164.
Gething, M-J. and Sambrook, J., "Cell-surface expression of influenza haemagglutinin from a cloned DNA copy of the RNA gene", Nature, 1981, 293:620-625.
Gilman, M.S.A., et al., "Characterization of a Prefusion-Specific Antibody That Recognizes a Quaternary, Cleavage-Dependent Epitope on the RSV Fusion Glycoprotein", PLoS Pathogens, 2015, 11(7):e1005035, 17 pages.
Graham, F.L. and Van Der Eb, A.J., "A New Technique for the Assay of Infectivity of Human Adenovirus 5 DNA", Virology, 1973, 52:456-467.
Graham, F.L., et al., "Characteristics of a Human Cell Line Transformed by DNA from Human Adenovirus Type 5", J. Gen. Virol., 1977, 36(1):59-74.
Haj-Ahmad, Y. and Graham, F.L., "Development of a Helper-Independent Human Adenovirus Vector and Its Use in the Transfer of the Herpes Simplex Virus Thymidine Kinase Gene", Journal of Virology, 1986, 57(1):267-274.
Hermonat, P.L. and Muzyczka, N., "Use of adeno-associated virus as a mammalian DNA cloning vector: Transduction of neomycin resistance into mammalian tissue culture cells", Proc. Natl. Acad. Sci. USA, 1984, 81(20):6466-6470.
Herz, J. and Gerard, R.D., "Adenovirus-mediated transfer of low density lipoprotein receptor gene acutely accelerates cholesterol clearance in normal mice", Proc. Natl. Acad. Sci. USA, 1993, 90(7):2812-2816.
International Preliminary Report on Patentability issued in PCT/IB2021/058995; mailed on Apr. 13, 2023; 11 pp.
Katayama, M., et al., "Primary Culture of Human Esophageal Epithelial Cells", The Tohoku Journal of Medicine, 1984, 143(2):129-140.
Kaufman, R.J., et al., "Translational efficiency of polycistronic mRNAs and their utilization to express heterologous genes in mammalian cells", The EMBO Journal, 1987, 6(1):187-193.
Keown, W.A., et al., "Methods for Introducing DNA into Mammalian Cells", Methods in Enzymology, 1990, 185:527-537.
Lemarchand, P., et al., "Adenovirus-mediated transfer of a recombinant human alpha1-antitrypsin cDNA to human endothelial cells", Proc. Natl. Acad. Sci. USA, 1992, 89(14):6482-6486.
Mader, S. and White, J.H., "A steroid-inducible promoter for the controlled overexpression of cloned genes in eukaryotic cells", Proc. Natl. Acad. Sci. USA, 1993, 90:5603-5607.
Manome, Y., et al., "Coinduction of c-jun Gene Expression and Internucleosomal DNA Fragmentation by Ionizing Radiation", Biochemistry, 1993, 32:10607-10613.
Mansour, S.L., et al., "Disruption of the proto-oncogene int-2 in mouse embryo-derived stem cells: a general strategy for targeting mutations to non-selectable genes", Nature, 1988, 336:348-352.
Mantei, N., et al., "Rabbit beta-globin mRNA production in mouse L cells transformed with cloned rabbit beta-globin chromosomal DNA", Nature, 1979, 281:40-46.
Mather, J.P., "Establishment and Characterization of Two Distinct Mouse Testicular Epithelial Cell Lines", Biology of Reproduction, 1980, 23:243-252.
Mather, J.P., et al., "Culture of Testicular Cells in Hormone-Supplemented Serum-Free Medium", Annals New York Academy of Sciences, 1982, 383:44-68.
McLaughlin, S.K., et al., "Adeno-Associated Virus General Transduction Vectors: Analysis of Proviral Structures", Journal of Virology, 1988, 62(6):1963-1973.
McLellan et al., "Structure of RSV Fusion Glycoprotein Trimer Bound to a Prefusion-Specific Neutralizing Antibody", Science, 2013, 340:1113-1117.
Miller, A.D., "Progress Toward Human Gene Therapy", Blood, 76(2):271-278.
Muzyczka, N., "Use of Adeno-Associated Virus as a General Transduction Vector for Mammalian Cells", Current Topics in Microbiology and Immunology, 1992, 158:97-129.
NCBI GenBank GI: P138250; Swiss-Prot: P13843.1, https://www.ncbi.nlm.nih.gov/protein/138250, downloaded Mar. 25, 2026, 6 pages.
NCBI GenBank GI: P138251; Swiss-Prot: P03420.1, https://www.ncbi.nlm.nih.gov/protein/138251, downloaded Mar. 25, 2026, 14 pages.
Ngwuta, J.O., et al., "Prefusion F-specific antibodies determine the magnitude of RSV neutralizing activity in human sera", Science Translational Medicine, 2015, 7(309):309ra162, 10 pages.
Ogun, S.A., et al., "The Oligomerization Domain of C4-Binding Protein (C4bp) Acts as an Adjuvant, and the Fusion Protein Comprised of the 19-Kilodalton Merozite Surface Protein 1 Fused with the Murine C4bp Domain Protects Mice against Malaria", Infection and Immunity, 2008, 76(8):3817-3823.
Okayama, H. and Berg, P., "Bacteriophage Lambda Vector for Transducing a cDNA Clone Library into Mammalian Cells", Molecular and Cellular Biology, 1985, 5(5):1136-1142.
Quantin, B., et al., "Adenovirus as an expression vector in muscle cells in vivo", Proc. Natl. Acad. Sci. USA, 1992, 89(7):2581-2584.
Rosenfeld, M.A., "In Vivo Transfer of the Human Cystic Fibrosis Transmembrane Conductase Regulator Gene to the Airway Epithelium", Cell, 1992, 68(1):143-155.
Rosenfeld, M.A., et al., "Adenovirus-Mediated Transfer of a Recombinant alpha1-Antitrypsin Gene to the Lung Epithelium in Vivo", 1991, 252(5004):431-434.
Samulski, R.J., et al., "Helper-Free Stocks of Recombinant Adeno-Associated Viruses: Normal Integration Does Not Require Viral Gene Expression", Journal of Virology, 63(9):3822-3828.
Seed, B., "An LFA-3 cDNA encodes a phospholipid-linked membrane protein homologous to its receptor CD2", Nature, 1987, 329(6142):840-842.
Spencer, D.M., et al., "Controlling Signal Transduction with Synthetic Ligands", Science, 1993, 262(5136):1019-1024.
Thomas, K.R. and Capecchi, M.R., "Site-Directed Mutagenesis by Gene Targeting in Mouse Embryo-Derived Stem Cells", Cell, 1987, 51(3):503-512.
Tratschin, J-D., et al., "Adeno-Associated Virus Vector for High-Frequency Integration, Expression, and Rescue of Genes in Mammalian Cells", Molecular and Cellular Biology, 1985, 5(11):3251-3260.
Tratschin, J-D., et al., "Genetic Analysis of Adeno-Associated Virus: Properties of Deletion Mutants Constructed In Vitro and Evidence for an Adeno-Associated Virus Replication Function", 1984, 51(3):611-619.
Urlaub, G. and Chasin, L.A., "Isolation of Chinese hamster cell mutants deficient in dihydrofolate reductase activity", Proc. Natl. Acad. Sci. USA, 1980, 77(7):4216-4220.
Verkhovskaya, L.Z., et al., "The Effect of Glycerol Alcoxy-Derivatives on Morphological and Functional Properties of Continuous Cell Culture", Cryobiology, 1990, p. 33.
Wilson et al, "Hepatocyte-directed Gene Transfer in Vivo Leads to Transient Improvement of Hypercholesterolemia in Low Density Lipoprotein Receptor-deficient Rabbits", The Journal of Biological Chemistry 267(2):963-967 (1992).
Wondisford, F.E., et al., "Cloning of the Human Thyrotropin Beta-Subunit Gene and Transient Expression of Biologically Active Human Thyrotropin after Gene Transfection", Molecular Endocrinology, 1988, 2:32-39.
Written Opinion issued in PCT/IB2021/058995; mailed on Feb. 2, 2022; 9 pp.

(56) References Cited

OTHER PUBLICATIONS

Wu, G.Y. and Wu, C.H., "Receptor-mediated Gene Delivery and Expression in Vivo", The Journal of Biological Chemistry, 1988, 263(29):14621-14624.
Yoon, S.K., et al., "Adaptation of Chinese hamster ovary cells to low culture temperature: Cell growth and recombinant protein production", Journal of Biotechnology, 2006, 122(4):463-472.
Yunus, A.S., et al., "Elevated temperature triggers human respiratory syncytial virus F protein six-helix bundle formation", Virology, 2010, 396(2):226-237.

RSV F (A)
Harvest Host Cell Protein

RSV F (B)
Harvest Host Cell Protein

CELL CULTURE PROCESS FOR PRODUCING RSV F PROTEIN

REFERENCE TO SEQUENCE LISTING

This application is being filed electronically via EFS-Web and includes an electronically submitted sequence listing in .txt format. The .txt file contains a sequence listing entitled "PC072609A_SequenceListing_ST25_032923.txt" created on Mar. 29, 2023 and having a size of 13 KB. The sequence listing contained in this .txt file is part of the specification and is herein incorporated by reference in its entirety.

FIELD OF THE INVENTION

The invention relates to methods for producing an RSV F protein trimer in a fed batch cell culture.

BACKGROUND

Respiratory syncytial virus, or RSV, is a respiratory virus that infects the lungs and breathing passages. RSV is the leading cause of serious viral lower respiratory tract illness in infants worldwide and an important cause of respiratory illness in the elderly. However, no vaccines have been approved for preventing RSV infection.

RSV is a member of the Paramyxoviridae family. Its genome consists of a single-stranded, negative-sense RNA molecule that encodes 11 proteins, including nine structural proteins (three glycoproteins and six internal proteins) and two non-structural proteins. The structural proteins include three transmembrane surface glycoproteins: the attachment protein G, fusion protein F, and the small hydrophobic SH protein. There are two subtypes of RSV, A and B. They differ primarily in the G glycoprotein, while the sequence of the F glycoprotein is more conserved between the two subtypes.

The mature F glycoprotein has three general domains: ectodomain (ED), transmembrane domain (TM), and a cytoplasmic tail (CT). CT contains a single palmitoylated cysteine residue.

The F glycoprotein of human RSV is initially translated from the mRNA as a single 574-amino acid polypeptide precursor (referred to "F0" or "F0 precursor"), which contains a signal peptide sequence (amino acids 1-25) at the N-terminus. Upon translation the signal peptide is removed by a signal peptidase in the endoplasmic reticulum. The remaining portion of the F0 precursor (i.e., residues 26-574) may be further cleaved at two polybasic sites (a.a. 109/110 and 136/137) by cellular proteases (in particular furin), removing a 27-amino acid intervening sequence designated pep27 (amino acids 110-136) and generating two linked fragments designated F1 (C-terminal portion; amino acids 137-574) and F2 (N-terminal portion; amino acids 26-109). F1 contains a hydrophobic fusion peptide at its N-terminus and two heptad-repeat regions (HRA and HRB). HRA is near the fusion peptide, and HRB is near the TM domain. The F1 and F2 fragments are linked together through two disulfide bonds. Either the uncleaved F0 protein without the signal peptide sequence or a F1-F2 heterodimer can form a RSV F protomer. Three such protomers assemble to form the final RSV F protein complex, which is a homotrimer of the three protomers.

The F proteins of subtypes A and B are about 90 percent identical in amino acid sequence. An example sequence of the F0 precursor polypeptide for the A subtype is provided in SEQ ID NO: 1 (A2 strain; GenBank GI: 138251; Swiss Prot P03420), and for the B subtype is provided in SEQ ID NO: 2 (18537 strain; GenBank GI: 138250; Swiss Prot P13843). SEQ ID NO: 1 and SEQ ID NO:2 are both 574 amino acid sequences. The signal peptide sequence for SEQ ID NO: 1 and SEQ ID NO:2 has also been reported as amino acids 1-25 (GenBank and UniProt). In both sequences the TM domain is from approximately amino acids 530 to 550, but has alternatively been reported as 525-548. The cytoplasmic tail begins at either amino acid 548 or 550 and ends at amino acid 574, with the palmitoylated cysteine residue located at amino acid 550.

One of the primary antigens explored for RSV subunit vaccines is the F protein. The RSV F protein trimer mediates fusion between the virion membrane and the host cellular membrane and also promotes the formation of syncytia. In the virion prior to fusion with the membrane of the host cell, the largest population of F molecules forms a lollipop-shaped structure, with the TM domain anchored in the viral envelope [Dormitzer, P. R., Grandi, G., Rappuoli, R., Nature Reviews Microbiol, 10, 807, 2012.]. This conformation is referred to as the pre-fusion conformation. Pre-fusion RSV F is recognized by monoclonal antibodies (mAbs) D25, AM22, and MPE8, without discrimination between oligomeric states. Pre-fusion F trimers are specifically recognized by mAb AM14 [Gilman M S, Moin S M, Mas V et al. Characterization of a prefusion-specific antibody that recognizes a quaternary, cleavage-dependent epitope on the RSV fusion glycoprotein. PLoS Pathogens, 11(7), 2015]. During RSV entry into cells, the F protein rearranges from the pre-fusion state (which may be referred to herein as "pre-F"), through an intermediate extended structure, to a post-fusion state ("post-F"). During this rearrangement, the C-terminal coiled-coil of the pre-fusion molecule dissociates into its three constituent strands, which then wrap around the globular head and join three additional helices to form the post-fusion six helix bundle. If a pre-fusion RSV F trimer is subjected to increasingly harsh chemical or physical conditions, such as elevated temperature, it undergoes structural changes. Initially, there is loss of trimeric structure (at least locally within the molecule), and then rearrangement to the post-fusion form, and then denaturation of the domains.

To prevent viral entry, F-specific neutralizing antibodies presumably must bind the pre-fusion conformation of F on the virion, or potentially the extended intermediate, before the viral envelope fuses with a cellular membrane. Thus, the pre-fusion form of the F protein is considered the preferred conformation as the desired vaccine antigen [Ngwuta, J. O., Chen, M., Modjarrad, K., Joyce, M. G., Kanekiyo, M., Kumar, A., Yassine, H. M., Moin, S. M., Killikelly, A. M., Chuang, G. Y., Druz, A., Georgiev, I. S., Rundlet, E. J., Sastry, M., Stewart-Jones, G. B., Yang. Y., Zhang, B., Nason, M. C., Capella, C., Peeples, M., Ledgerwood, J. E., Mclellan, J. S., Kwong, P. D., Graham, B. S., Science Translat. Med., 14, 7, 309 (2015)]. Upon extraction from a membrane with surfactants such as Triton X-100, Triton X-114, NP-40, Brij-35, Brij-58, Tween 20, Tween 80, Octyl glucoside, Octyl thioglucoside, SDS, CHAPS, CHAPSO, or expression as an ectodomain, physical or chemical stress, or storage, the F glycoprotein readily converts to the post-fusion form [McLellan J S, Chen M, Leung S et al. Structure of RSV fusion glycoprotein trimer bound to a pre-fusion-specific neutralizing antibody. Science 340, 1113-1117 (2013); Chaiwatpongsakorn, S., Epand, R. F., Collins, P. L., Epand R. M., Peeples, M. E., J Virol. 85(8):3968-77 (2011); Yunus, A. S., Jackson T. P., Crisafi, K., Burimski, I., Kilgore, N. R., Zoumplis, D., Allaway, G. P., Wild, C. T., Salzwedel, K. Virology. 2010 Jan. 20; 396(2):226-37]. Therefore, the preparation of pre-fusion F as a vaccine antigen has remained a challenge. Since the neutralizing and protective antibodies function by interfering with virus entry, it is postulated that an F antigen that elicits only post-fusion specific antibodies is not expected to be as effective as an F antigen that elicits pre-fusion specific antibodies. Therefore, it is considered more desirable to utilize an F protein vaccine that contains a F protein immunogen in the pre-fusion form (or potentially the extended intermediate form). Mutants of the RSV F protein have been provided to increase the stability of the pre fusion form of the protein (see for example PCT application No WO2017/109629) and are promising vaccine candidate. Therefore, there is a need for a process to produce these antigens in the desired trimer conformation and with a suitable titer. Such process should also be sufficiently robust to be used at large scale. In addition, the amount of host cell proteins (HCP) or other impurities should be minimized in order to facilitate the downstream processing of the produced trimers.

SUMMARY OF THE INVENTION

The invention relates to a method for producing an RSV F protein trimer in a fed batch cell culture, said method comprising the steps of:

(i) providing mammalian cells that contain a gene encoding an RSV F protein in a cell culture medium to start a cell culture, and, (ii) culturing the cells at a temperature between about 33.0° C. and 35.0° C., and (iii) providing glucose in a restricted manner to the cell culture by feeding glucose to the cell culture in response to rise of pH above a predetermined pH value.

In some embodiments the method comprises a temperature shift where the temperature is shifted to a lower temperature between about 30.0 and about 32.0° C., preferably about 31.0° C.

DETAILED DESCRIPTION OF THE INVENTION

Figure 1A:
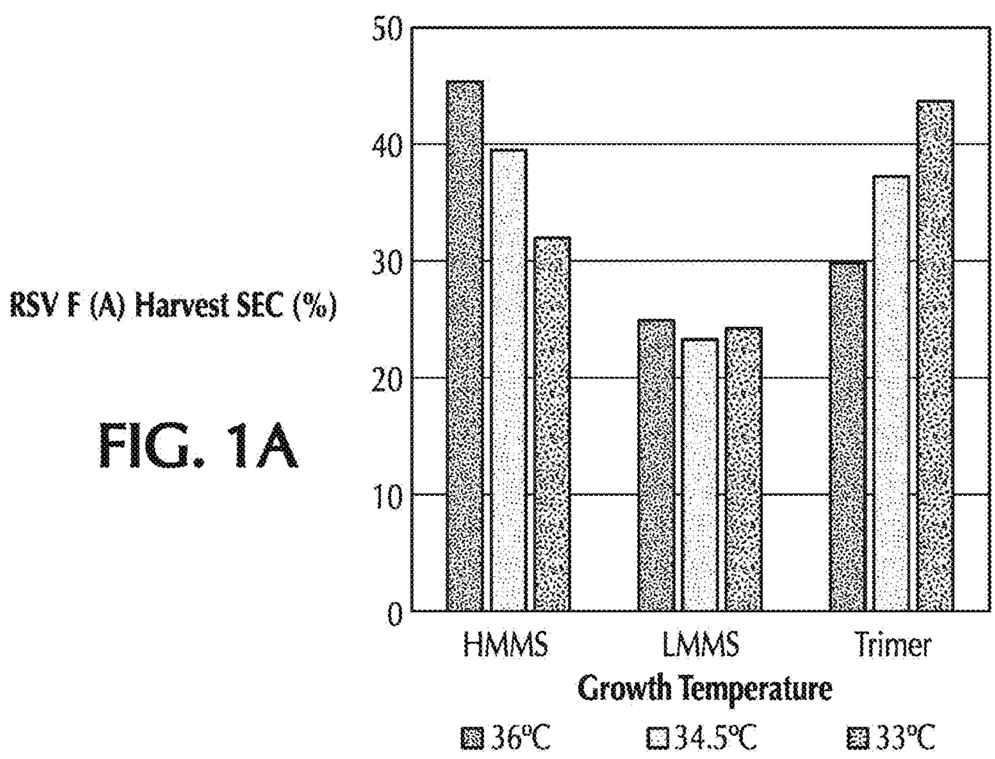
FIG. 1A shows the effect of the growth temperature on the percentage of HMMS, LMMS and RSV F protein of subtype A trimer as measured by size exclusion chromatography.
Figure 1B:
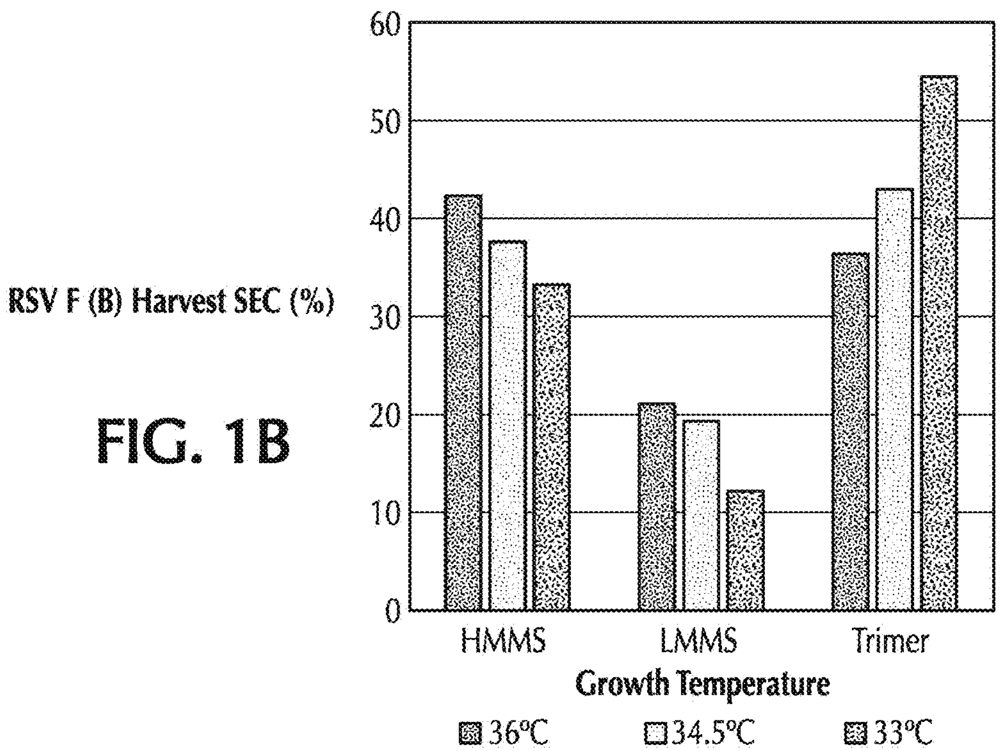
FIG. 1B shows the effect of the growth temperature on the percentage of HMMS, LMMS and RSV F protein of subtype B trimer as measured by size exclusion chromatography

The invention relates to a method for producing an RSV F protein trimer in a fed batch cell culture, said method comprising the steps of:

(i) providing mammalian cells that contain a gene encoding an RSV F protein in a cell culture medium to start a cell culture, and, (ii) culturing the cells at a temperature between about 33.0° C. and about 35.0° C., and (iii) providing glucose in a restricted manner to the cell culture by feeding glucose to the cell culture in response to rise of pH above a predetermined pH value.

The method of the invention is particularly useful for producing RSV F protein trimers to be used as antigens in immunogenic compositions. The method of the invention can be used for manufacturing RSV F protein trimers at large scale, for example in cell culture medium volume of at least 500 L or even at least 3000 L. The method of the invention provides high titers and high percentages of RSV protein F in the form of trimers while also minimizing the amount of HCP or other impurities thereby facilitating further downstream processing. In addition, specific conditions optimizing the processing of the protein have been identified and can be used in the method of the invention.

In some embodiments, the RSV F protein is an RSV F protein of subtype A. In some embodiments, the RSV F protein is an RSV F protein of subtype B. In some embodiments, the RSV F protein is a mutant of wild type RSV F protein. In some embodiments, the RSV F protein is a mutant of wild type RSV F protein of subtype A. In some embodiments, the RSV F protein is a mutant of wild type RSV F protein of subtype B. In some embodiments, the mutants display introduced mutations in the amino acid sequence relative to the amino acid sequence of the corresponding wild-type RSV F protein and are immunogenic against the wild-type RSV F protein or against a virus comprising the wild-type F protein. The amino acid mutations in the mutants include amino acid substitutions, deletions, or additions relative to a wild-type RSV F protein.

In some embodiments, the RSV F protein produced by the method of the invention is an RSV protein mutant as disclosed in WO2017/109629 which is incorporated herein by reference.

In some embodiments, the RSV F protein is a mutant of a wild-type RSV F protein, wherein the introduced amino acid mutations are mutation of a pair of amino acid residues in a wild-type RSV F protein to a pair of cysteines ("engineered disulfide mutation"). The introduced pair of cysteine residues allows for formation of a disulfide bond between the cysteine residues that stabilize the protein's conformation or oligomeric state, such as the pre-fusion conformation. Examples of specific pairs of such mutations include: 55C and 188C; 155C and 290C; 103C and 148C; and 142C and 371C, such as S55C and L188C; S155C and S290C; T103C and I148C; and L142C and N371C.

In still other embodiments, the RSV F protein mutants comprise amino acid mutations that are one or more cavity filling mutations. Examples of amino acids that may be replaced with the goal of cavity filling include small aliphatic (e.g. Gly, Ala, and Val) or small polar amino acids (e.g. Ser and Thr) and amino acids that are buried in the pre-fusion conformation, but exposed to solvent in the post-fusion conformation. Examples of the replacement amino acids include large aliphatic amino acids (lie, Leu and Met) or large aromatic amino acids (His, Phe, Tyr and Trp). In some specific embodiments, the RSV F protein mutant comprises a cavity filling mutation selected from the group consisting of:

(1) substitution of S at positions 55, 62, 155, 190, or 290 with I, Y, L, H, or M;

(2) substitution of T at position 54, 58, 189, 219, or 397 with I, Y, L, H, or M;

(3) substitution of G at position 151 with A or H;

(4) substitution of A at position 147 or 298 with I, L, H, or M;

(5) substitution of V at position 164, 187, 192, 207, 220, 296, 300, or 495 with I, Y, H; and (6) substitution of R at position 106 with W.

In some particular embodiments, the RSV F protein mutant comprises at least one cavity filling mutation selected from the group consisting of: T54H, S190I, and V296I.

In still other embodiments, the RSV F protein mutants comprise electrostatic mutations, which decrease ionic repulsion or increase ionic attraction between resides in a protein that are proximate to each other in the folded structure. In several embodiments, the RSV F protein mutant includes an electrostatic substitution that reduces repulsive ionic interactions or increases attractive ionic interactions with acidic residues of Glu487 and Asp489 from another protomer of RSV F trimer. In some specific embodiments, the RSV F protein mutant comprises an electrostatic mutation selected from the group consisting of:

(1) substitution of E at position 82, 92, or 487 by D, F, Q, T, S, L, or H;

(2) substitution of K at position 315, 394, or 399 by F, M, R, S, L, I, Q, or T;

(3) substitution of D at position 392, 486, or 489 by H, S, N, T, or P; and (4) substitution of R at position 106 or 339 by F, Q, N, or W.

In still other embodiments, the RSV F protein mutants comprise a combination of two or more different types of mutations selected from engineered disulfide mutations, cavity filling mutations, and electrostatic mutations. In some particular embodiments, the RSV F protein mutants comprise a combination of mutations relative to the corresponding wild-type RSV F protein, wherein the combination of mutations is selected from the group consisting of:

(1) combination of T103C, I148C, S190I, and D486S;
(2) combination of T54H S55C L188C D486S;
(3) combination of T54H, T103C, I148C, S190I, V296I, and D486S;
(4) combination of T54H, S55C, L142C, L188C, V296I, and N371C;
(5) combination of S55C, L188C, and D486S;
(6) combination of T54H, S55C, L188C, and S190I;
(7) combination of S55C, L188C, S190I, and D486S;
(8) combination of T54H, S55C, L188C, S190I, and D486S;
(9) combination of S155C, S190I, S290C, and D486S;
(10) combination of T54H, S55C, L142C, L188C, V296I, N371C, D486S, E487Q, and D489S; and
(11) combination of T54H, S155C, S190I, S290C, and V296I.

In some embodiments, the RSV F protein is of subtype A and comprises the mutations T103C, I148C, S190I, and D486S.

In some embodiments, the RSV F protein is of subtype B and comprises the mutations T103C, I148C, S190I, and D486S.

In view of the substantial conservation of RSV F sequences, a person of ordinary skill in the art can easily compare amino acid positions between different native RSV F sequences to identify corresponding RSV F amino acid positions between different RSV strains and subtypes. For example, across nearly all identified native RSV F0 precursor proteins, the furin cleavage sites fall in the same amino acid positions. Thus, the conservation of native RSV F protein sequences across strains and subtypes allows use of a reference RSV F sequence for comparison of amino acids at particular positions in the RSV F protein. For the purposes of this disclosure (unless context indicates otherwise), the RSV F protein amino acid positions are given with reference to the amino acid sequence of the full length native F precursor polypeptide of the RSV A2 strain; corresponding to GenInfo Identifier GI 138251 and Swiss Prot identifier P03420.

In some embodiments, the RSV F protein produced by the method of the invention is an RSV protein mutant as disclosed WO2009/079796, WO2010/149745, WO2011/008974, WO2014/160463, WO2014/174018, WO2014/202570, WO2015/013551, WO2015/177312, WO2017/005848 and WO2018/109220. The RSV F proteins disclosed in these references are incorporated herein by reference.

The term "fed-batch culture" as used herein refers to a method of culturing cells in which additional components are provided to the culture at a time or times subsequent to the beginning of the culture process. In some embodiments, these additional components are provided together in a feed medium. Such provided components typically comprise nutritional components for the cells which have been depleted during the culturing process. A fed-batch culture is typically stopped at some point and the cells and/or components in the medium are harvested and optionally purified. In some embodiments, the fed-batch culture comprises a basal medium supplemented with a feed medium.

In some embodiments, the cells are cultured at a temperature of 33.0° C., 33.1° C., 33.2° C., 33.3° C., 33.4° C., 33.5° C., 33.6° C., 33.7° C., 33.8° C., 33.9° C., 34.0° C., 34.1° C., 34.2° C., 34.3° C., 34.4° C., 34.5° C., 34.6° C., 34.7° C., 34.8° C., 34.9° C. or 35.0° C. In a preferred embodiment, the cells are cultured at a temperature between 34.0° C. and 35.0° C. In a preferred embodiment, the cells are cultured at a temperature of 34.5° C.

The method of the invention comprises a step of providing glucose in a restricted manner to the cells wherein glucose is fed to the cells in response to a rise of pH above a predetermined pH value. Such method of feeding glucose depending on pH variations is also referred to as HiPDOG and is disclosed for example in WO2004/104186 and in Gagnon et al ((2011) (Biotechnology and bioengineering 108: 1328-1337), which are both incorporated herein by reference.

In some embodiments, a pH sensor is used to monitor pH of the cell culture.

In some embodiments, the predetermined pH value of the method of the invention corresponds to an increase of 0.01 to 0.10 such as for example 0.01, 0.02, 0.03, 0.04, 0.05, 0.06, 0.07, 0.08, 0.09 or 0.10 above the pH set point of the culture. In some embodiments, the predetermined pH value corresponds to an increase of 0.05 above the pH set point of the culture.

In some embodiments, the pH set point of the cell culture is between 6.70 and 7.30. In some embodiments, the pH set point of the cell culture is between 6.90 and 7.20. In some embodiments, the pH set point of the cell culture is between 7.00 and 7.10. In a preferred embodiment, the pH set point of the cell culture is 7.05.

In a preferred embodiment, the pH set point of the cell culture is 7.05 and the predetermined pH value corresponds to an increase of 0.05 above said set point.

In some embodiments, during the phase of the cell culture where glucose is provided in a restricted manner, the pH of the cell culture is between 6.70 and 7.30. In some embodiments, during the phase of the cell culture where glucose is provided in a restricted manner, the pH of the cell culture is between 6.90 and 7.20. In some embodiments, during the phase of the cell culture where glucose is provided in a restricted manner, the pH set point is 6.95. In some embodiments, during the phase of the cell culture where glucose is provided in a restricted manner, the pH set point is 7.07. In some embodiments, during the phase of the cell culture where glucose is provided in a restricted manner, the pH set point is 7.01. In some embodiments, during the phase of the cell culture where glucose is provided in a restricted manner, the pH set point is 7.20.

In some embodiments, after the phase of the cell culture where glucose is provided in a restricted manner, the pH set point is 7.20. In some embodiments, after the phase of the cell culture where glucose is provided in a restricted manner, the pH set point is 7.20 and the pH operating range is 7.05 to 7.35. In some embodiments, after the phase of the cell culture where glucose is provided in a restricted manner, the pH set point is 6.90. In some embodiments, after the phase of the cell culture where glucose is provided in a restricted manner, the pH set point is 6.90 and the pH operating range is 6.75 to 7.05.

In some embodiments, feeding glucose to the cell culture in response to rise of pH above a predetermined pH value comprises feeding glucose until the pH decreases to reach the pH set point of the culture.

In some embodiments, glucose is provided in a restricted manner to the cell culture during the growth phase of the culture. In some embodiments, glucose is provided in a restricted manner to the cell culture for 1 to 6 days, preferably 3, 4 or 5 days, more preferably for 4 or 5 days.

In some embodiments, the step of providing glucose in a restricted manner to the cell culture starts on day 0, day 1 or day 2.

In some embodiments, when glucose is provided in a restricted manner, it is provided as an independent feed i.e not comprising other components of the feed medium.

In some embodiments, when glucose is provided in a restricted manner, it is provided as part of the feed medium.

In some embodiments of the method disclosed herein, the temperature is shifted to a lower temperature between about 30.0° C. and about 32.0° C., preferably about 31.0° C. In some embodiments, the temperature is shifted to a lower temperature between day 3 and day 7 (i.e between the third day of culture and the seventh day of culture). In a preferred embodiment, the temperature is shifted to a lower temperature on day 5 or on day 6. In a preferred embodiment the temperature is shifted to a lower temperature after the provision of glucose in a restricted manner is stopped.

In some embodiments, the method of the invention results in an improved titer as compared to other methods such as for example methods conducted at a temperature higher or lower than the temperature or temperature ranges defined herein and/or methods without temperature shift and/or methods using a medium comprising glucocorticoids and/or methods not comprising a step of providing glucose in a restricted manner to the cell culture by feeding glucose to the cell culture in response to rise of pH above a predetermined pH value. Titer can be determined by any method known in the art. In one embodiment, titer is measured by reverse phase high-performance liquid chromatography (RP-HPLC).

In some embodiments, the method of the invention results in an increased percentage of trimer and a reduced percentage high molecular mass species (HMMS) and/or low molecular mass species (LMMS) as compared to other methods such as for example methods conducted at a temperature higher or lower than the temperature or temperature ranges defined herein and/or methods without temperature shift and/or methods using a medium comprising glucocorticoids and/or methods not comprising a step of providing glucose in a restricted manner to the cell culture by feeding glucose to the cell culture in response to rise of pH above a predetermined pH value. Percentage of trimer, HMMS and LMMS can be determined by any method known in the art. In some embodiments, percentage of trimer, HMMS and LMMS are measured by size exclusion chromatography (SEC-HPLC).

In some embodiments, the method of the invention results in an increased triter as compared to other methods such as for example methods conducted at a temperature higher or lower than the temperature or temperature ranges defined herein and/or methods without temperature shift and/or methods using a medium comprising glucocorticoids and/or methods not comprising a step of providing glucose in a restricted manner to the cell culture by feeding glucose to the cell culture in response to rise of pH above a predetermined pH value. Triter values are calculated by multiplying percentage of trimer, preferably as obtained by SEC-HPLC, by titer, preferably obtained by RP-HPLC. Triter provides an estimate of how much protein is produced in the trimeric form.

In some embodiments, the method of the invention results in a reduced amount of Host Cell Protein as compared to other methods such as for example methods conducted at a temperature higher or lower than the temperature or temperature ranges defined herein and/or methods without temperature shift and/or methods using a medium comprising glucocorticoids and/or methods not comprising a step of providing glucose in a restricted manner to the cell culture by feeding glucose to the cell culture in response to rise of pH above a predetermined pH value. HCP can be measured by any method known in the art. In some embodiments, HCP was measured by enzyme-linked immunoassay (ELISA).

In some embodiments, the method of the invention results in an improved amount of processed RSV F (A) or RSV F (B) in a form suitable for forming trimers that can be used as antigens in immunogenic compositions as compared to other methods such as for example methods conducted at a temperature higher or lower than the temperature or temperature ranges defined herein and/or methods without temperature shift and/or methods using a medium comprising glucocorticoids and/or methods not comprising a step of providing glucose in a restricted manner to the cell culture by feeding glucose to the cell culture in response to rise of pH above a predetermined pH value. Amount of processed RSV F (A) or RSV F (B) in a suitable form can be determined by any method known in the art. In one embodiment, such amount is measured by western blot, for example as shown in example 3.

In some embodiments, the method of the invention results in an improved titer and/or an increased percentage of trimer and a reduced percentage high molecular mass species (HMMS) and/or low molecular mass species (LMMS) and/or a reduced amount of Host Cell Protein as compared to other methods such as for example methods conducted at a temperature higher or lower than the temperature or temperature ranges defined herein and/or methods without temperature shift and/or methods using a medium comprising glucocorticoids and/or methods not comprising a step of providing glucose in a restricted manner to the cell culture by feeding glucose to the cell culture in response to rise of pH above a predetermined pH value.

The terms "medium", "cell culture medium" and "culture medium" as used herein refer to a solution containing nutrients which nourish growing mammalian cells. Typically, such solutions provide essential and non-essential amino acids, vitamins, energy sources, lipids, and trace elements required by the cell for minimal growth and/or survival. In one embodiment, the medium may comprise Ala, Arg, Asn, Asp, Glu, Gly, His, lie, Leu, Lys, Met, Phe, Pro, Ser, Thr, Trp, Tyr, Val and Cystine and/or Cys.

Such a solution may also contain supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), inorganic compounds present at high final concentrations (e.g., iron), amino acids, lipids, and/or glucose or other energy source. In some embodiments, a medium is advantageously formulated to a pH and salt concentration optimal for cell survival and proliferation. For example, the medium may be formulated to a pH between around 7.1 and 7.3 and a final osmolality between around 1000 and 1300 mOsm.

Example of known basal and/or feed cell culture media which can be used in the method of the invention include those disclosed in WO2006/026445, WO2008/109410, WO2008/063892, EP2243827, WO2002/066603, WO2015/140708 and WO2006/050050.

In a preferred embodiment, the feed medium used in the method of the invention comprises 4 to 10 mM Ala, 30 to 60 mM Arg, 50 to 90 mM Asn, 10 to 30 mM Asp, 2 to 40 mM Glu, 2 to 15 mM Gly, 8 to 20 mM His, 25 to 32 mM Ile, 35 to 60 mM Leu, 28 to 60 mM Lys, 9 to 25 mM Met, 10 to 30 mM Phe, 15 to 40 mM Pro, 44 to 80 mM Ser, 20 to 45 mM Thr, 2 to 10 mM Trp and 20 to 50 mM Val.

In some embodiments, the medium is a chemically defined medium, wherein the components of the medium are both known and controlled. In some embodiments, the medium is a complex medium, in which not all components of the medium are known and/or controlled.

Chemically defined growth media for mammalian cell culture have been extensively developed and published over the last several decades. All components of defined media are well characterized, and so defined media do not contain complex additives such as serum or hydrolysates. Early media formulations were developed to permit cell growth and maintenance of viability with little or no concern for protein production. More recently, media formulations have been developed with the express purpose of supporting highly productive recombinant protein producing cell cultures. Such media are preferred for use in the method of the invention. Such media generally comprises high amounts of nutrients and in particular of amino acids to support the growth and/or the maintenance of cells at high density. If necessary, these media can be modified by the skilled person for use in the method of the invention.

Not all components of complex media are well characterized, and so complex media may contain additives such as simple and/or complex carbon sources, simple and/or complex nitrogen sources, and serum, among other things. In some embodiments, complex media suitable for the present invention contains additives such as hydrolysates in addition to other components of defined medium as described herein.

In some embodiments, defined media typically includes roughly fifty chemical entities at known concentrations in water. Some of them also contain one or more well-characterized proteins such as insulin, IGF-1, transferrin or BSA, but others require no protein components and so are referred to as protein-free defined media. Typical chemical components of the media fall into five broad categories: amino acids, vitamins, inorganic salts, trace elements, and a miscellaneous category that defies neat categorization.

Cell culture medium may be optionally supplemented with supplementary components. The term "supplementary components" as used herein refers to components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In some embodiments, supplementary components may be added to the initial cell culture. In some embodiments, supplementary components may be added after the beginning of the cell culture.

Typically, trace elements refer to a variety of inorganic salts included at micromolar or lower levels. For example, commonly included trace elements are zinc, selenium, copper, and others. In some embodiments, iron (ferrous or ferric salts) can be included as a trace element in the initial cell culture medium at micromolar concentrations. Manganese is also frequently included among the trace elements as a divalent cation ($MnCl_2$ or $MnSO_4$) in a range of nanomolar to micromolar concentrations. Numerous less common trace elements are usually added at nanomolar concentrations.

In some embodiments, the cell culture medium used in the method of the invention does not comprise glucocorticoid compounds.

Glucocorticoid compounds are known to modulate various cellular functions such as cell proliferation, metabolism, glycosylation, and secretion of many proteins and are therefore often included in cell culture media, in particular for use in large scale manufacturing process.

Examples of glucocorticoid compounds used as cell culture media components include, but are not limited to hydrocortisone, prednisone, prednisolone, methylprednisolone, dexamethasone, betamethasone, triamcinolone and fludrocortisone acetate.

As shown in below example 3, the presence of a glucocorticoid such as hydrocortisone in the cell culture medium has a detrimental effect on the amount of RSV F protein in the correct form. Without being bound by any theory, this effect may be due to an interference of the glucocorticoid compounds with the processing of the RSV F protein resulting in an increased amount of unprocessed RSV protein in the harvested material.

In some embodiments, the cell culture medium used in the methods of the invention does not comprise glucocorticoid compounds. In some embodiments, the basal medium used in the methods of the invention does not comprise glucocorticoid compounds. In some embodiments, the feed medium used in the methods of the invention does not comprise glucocorticoid compound. In some embodiments, the basal medium and the feed medium used in the methods of the invention do not comprise glucocorticoid compounds.

In some embodiments, the cell culture medium used in the methods of the invention does not comprise any of hydrocortisone, prednisone, prednisolone, methylprednisolone, dexamethasone, betamethasone, triamcinolone and fludrocortisone acetate. In some embodiments, the basal medium used in the methods of the invention does not comprise any of hydrocortisone, prednisone, prednisolone, methylprednisolone, dexamethasone, betamethasone, triamcinolone and fludrocortisone acetate. In some embodiments, the feed medium used in the methods of the invention does not comprise any of hydrocortisone, prednisone, prednisolone, methylprednisolone, dexamethasone, betamethasone, triamcinolone and fludrocortisone acetate. In some embodiments, the basal medium and the feed medium used in the methods of the invention do not comprise any of hydrocortisone, prednisone, prednisolone, methylprednisolone, dexamethasone, betamethasone, triamcinolone and fludrocortisone acetate.

In some embodiments, the cell culture medium used in the methods of the invention does not comprise any of hydrocortisone, prednisolone, betamethasone and dexamethasone. In some embodiments, the basal medium used in the methods of the invention does not comprise any of hydrocortisone, prednisolone, betamethasone and dexamethasone. In some embodiments, the feed medium used in the methods of the invention does not comprise any of hydrocortisone, prednisolone, betamethasone and dexamethasone. In some embodiments, the basal medium and the feed medium used in the methods of the invention do not comprise any of hydrocortisone, prednisolone, betamethasone and dexamethasone.

In some embodiments, the cell culture medium used in the methods of the invention does not comprise hydrocortisone. In some embodiments, the basal medium used in the methods of the invention does not comprise hydrocortisone. In some embodiments, the feed medium used in the methods of the invention does not comprise hydrocortisone. In some embodiments, the basal medium and the feed medium used in the methods of the invention do not comprise hydrocortisone.

In some embodiments, the medium used in the method of the invention is a medium suitable for supporting high viable cell density, such as for example $1\times10^6$ cells/mL, $5\times10^6$ cells/mL, $1\times10^7$ cells/mL, $5\times10^7$ cells/mL, $1\times10^8$ cells/mL or $5\times10^8$ cells/mL, in a cell culture. In some embodiments, the cell culture is a CHO cell fed-batch culture. In some embodiments, the cells are grown to a viable cell density greater than $1\times10^6$ cells/mL, $5\times10^6$ cells/mL, $1\times10^7$ cells/mL, $5\times10^7$ cells/mL, $1\times10^8$ cells/mL or $5\times10^8$ cells/mL.

The term "viable cell density" as used herein refers to the number of cells present in a given volume of medium. Viable cell density can be measured by any method known to the skilled person. Preferably, viable cell density is measured using an automated cell counter such as Bioprofile Flex®. The term maximum cell density as used herein refers to the maximum cell density achieved during the cell culture. The term "cell viability" as used herein refers to the ability of cells in culture to survive under a given set of culture conditions or experimental variations. Those of ordinary skill in the art will appreciate that one of many methods for determining cell viability are encompassed in this invention. For example, one may use a dye (e.g., trypan blue) that does not pass through the membrane of a living cell, but can pass through the disrupted membrane of a dead or dying cell in order to determine cell viability.

Cell Culture Methods

The terms "culture" and "cell culture" as used herein refer to a cell population that is suspended in a medium under conditions suitable to survival and/or growth of the cell population. As will be clear to those of ordinary skill in the art, in some embodiments, these terms as used herein refer to the combination comprising the cell population and the medium in which the population is suspended.

The term "fed-batch culture" or "fed-batch cell culture" as used herein refers to a method of culturing cells in which additional components are provided to the culture at a time or times subsequent to the beginning of the culture process. Such provided components typically comprise nutritional components for the cells which have been depleted during the culturing process. A fed-batch culture is typically stopped at some point and the cells and/or components in the medium are harvested and optionally purified. In some embodiments, the fed-batch culture comprises a basal medium supplemented with feed media.

Cells may be grown in any convenient volume chosen by the practitioner. For example, cells may be grown in small scale reaction vessels ranging in volume from a few milliliters to several liters. Alternatively, cells may be grown in large scale commercial bioreactors ranging in volume from at least 500, 1000, 2500, 5000, 8000, 10,000, 12,000, 15000, 20000 or 25000 liters or more, or any volume in between. In some embodiments, the volume of the cell culture is at least 500 L. In some embodiments, the volume of the cell culture is at least 3000 L.

In some embodiments, the cells may be grown during the initial growth phase (or growth phase) for a greater or lesser amount of time, depending on the needs of the practitioner and the requirement of the cells themselves. In some embodiments, the cells are grown for a period of time sufficient to achieve a predefined cell density. In some embodiments, the cells are grown for a period of time sufficient to achieve a predefined cell density of about $1\times10^6$ cells/mL, about $5\times10^6$ cells/mL, about $1\times10^7$ cells/mL, about $5\times10^7$ cells/mL, about $1\times10^8$ cells/mL or about $5\times10^8$ cells/mL. In some embodiments, the cells are grown for a period of time sufficient to achieve a cell density that is a given percentage of the maximal cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal cell density. In some embodiments, the cells are grown until the cell density does not increase by more than 15%, 14%, 13%, 12%, 11%, 10%, 9%, 8%, 7%, 6%, 5%, 4%, 3%, 2% or 1% per day of culture. In some embodiments, the cells are grown until the cell density does not increase by more than 5% per day of culture.

In some embodiments the cells are allowed to grow for a defined period of time. For example, depending on the starting concentration of the cell culture and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days, preferably for 4 to 10 days. The practitioner of the present invention will be able to choose the duration of the initial growth phase depending on protein production requirements and the needs of the cells themselves.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc.

In accordance with the present invention, one of ordinary skill in the art will understand that the temperature at which the cells are cultured is a temperature set point and is controlled during the cell culture to limit the variation of temperature around the set point.

A temperature shift to a lower temperature can be used in the method of the invention. In such case, one of ordinary skill in the art will understand that a lower temperature set point is defined and that once the temperature has reached the lower set point, it is controlled to limit the variation of temperature around said lower set point. When shifting the temperature of the culture, the temperature shift may be relatively gradual. For example, it may take several hours or days to complete the temperature change. Alternatively, the temperature shift may be relatively abrupt. For example, the temperature change may be complete in less than several hours. Given the appropriate production and control equipment, such as is standard in the commercial large-scale production of polypeptides or proteins, the temperature change may even be complete within less than an hour.

In some embodiments, once the conditions of the cell culture have been shifted as discussed above, the cell culture is maintained for a subsequent production phase under conditions conducive to the survival and viability of the cell culture and appropriate for expression of the desired polypeptide or protein at commercially adequate levels. In some embodiments, the cells may be maintained in the subsequent production phase until a desired cell density or production titer is reached. In some embodiments, the duration of the production phase is comprised between 2 and 10 days, i.e 2, 3, 4, 5, 6, 7, 8, 9 or 10 days, preferably between 4 to 8 days, preferably 6 days.

In some embodiment the duration of the growth phase is about 6 days and the duration of the production phase is about 6 days.

The cell culture may be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc.

Cells

Any mammalian cell susceptible to cell culture may be utilized in accordance with the present invention. Non-limiting examples of mammalian cells that may be used in accordance with the present invention include BALB/c mouse myeloma line (NSO/I, ECACC No: 85110503); human retinoblasts (PER. C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2). In some preferred embodiments, the cells are CHO cells. In some preferred embodiments, the cells are GS-CHO cells.

Expression of Proteins

As noted above, in many instances the cells will be selected or engineered to produce high levels of desired products. Often, cells will be manipulated by the hand of man to produce high levels of recombinant protein, for example by introduction of a gene encoding the protein of interest and/or by introduction of genetic control elements that regulate expression of that gene (whether endogenous or introduced).

Even amongst a population of cells of one particular type engineered to express a specific protein, variability within the cellular population exists such that certain individual cells will grow better, produce more protein of interest. In certain embodiments, a cell line is empirically selected by the practitioner for robust growth under the particular conditions chosen for culturing the cells. In some embodiments, individual cells engineered to express a particular protein are chosen for large-scale production based on cell growth, final cell density, percent cell viability, titer of the expressed protein or any combination of these or any other conditions deemed important by the practitioner.

The term "host cell" as used herein refers to a cell that is manipulated to produce a protein of interest as described herein. A protein may be expressed from a gene that is endogenous to the cell, or from a heterologous gene that is introduced into the cell. A protein may be one that occurs in nature, or may alternatively have a sequence that was engineered or selected by the hand of man.

Isolation of the Expressed Protein

In general, it will typically be desirable to isolate and/or purify proteins expressed according to the present invention. In certain embodiments, the expressed protein is secreted into the medium and thus cells and other solids may be removed, as by centrifugation or filtering for example, as a first step in the purification process.

The expressed protein may be isolated and purified by standard methods including, but not limited to, chromatography (e.g., ion exchange, affinity, size exclusion, and hydroxyapatite chromatography), gel filtration, centrifugation, or differential solubility, ethanol precipitation and/or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol. 182), Academic Press, 1997, each of which is incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the protein during the purification process. Protease inhibitors are particularly advantageous when cells must be lysed in order to isolate and purify the expressed protein.

One of ordinary skill in the art will appreciate that the exact purification technique will vary depending on the character of the protein to be purified, the character of the cells from which the protein is expressed, and/or the composition of the medium in which the cells were grown.

Introduction of Genes for the Expression of Proteins into Host Cells

Generally, a nucleic acid molecule introduced into the cell encodes the protein desired to be expressed according to the present disclosure.

Methods suitable for introducing nucleic acids sufficient to achieve expression of a protein of interest into mammalian host cells are known in the art. See, for example, Gething et al., *Nature,* 293:620-625, 1981; Mantei et al., *Nature,* 281:40-46, 1979; Levinson et al. EP 117,060; and EP 117,058, each of which is incorporated herein by reference. For mammalian cells, common methods of introducing genetic material into mammalian cells include the calcium phosphate precipitation method of Graham and van der Erb (*Virology,* 52:456-457, 1978) or the Lipofectamine™ (Gibco BRL) Method of Hawley-Nelson (*Focus* 15:73, 1993). General aspects of mammalian cell host system transformations have been described by Axel in U.S. Pat. No. 4,399,216 issued Aug. 16, 1983. For various techniques for introducing genetic material into mammalian cells, see Keown et al., *Methods in Enzymology,* 1989, Keown et al., *Methods in Enzymology,* 185:527-537, 1990, and Mansour et al., *Nature,* 336:348-352, 1988. In some embodiments, a nucleic acid to be introduced is in the form of a naked nucleic acid molecule. For example, the nucleic acid molecule introduced into a cell may consist only of the nucleic acid encoding the protein and the necessary genetic control elements. Alternatively, a nucleic acid encoding the protein (including the necessary regulatory elements) may be contained within a plasmid vector. Non-limiting representative examples of suitable vectors for expression of proteins in mammalian cells include pCDNA1; pCD, see Okayama, et al. Mol. Cell Biol. 5:1136-1142, 1985; pMClneo Poly-A, see Thomas, et al. Cell 51:503-512, 1987; a baculovirus vector such as pAC 373 or pAC 610; CDM8, see Seed, B. Nature 329:840, 1987; and pMT2PC, see Kaufman, et al. EMBO J. 6:187-195, 1987, each of which is incorporated herein by reference in its entirety. In some embodiments, a nucleic acid molecule to be introduced into a cell is contained within a viral vector. For example, a nucleic acid encoding the protein may be inserted into the viral genome (or a partial viral genome). Regulatory elements directing the expression of the protein may be included with the nucleic acid inserted into the viral genome (i.e., linked to the gene inserted into the viral genome) or can be provided by the viral genome itself.

Naked DNA can be introduced into cells by forming a precipitate containing the DNA and calcium phosphate. Alternatively, naked DNA can also be introduced into cells by forming a mixture of the DNA and DEAE-dextran and incubating the mixture with the cells or by incubating the cells and the DNA together in an appropriate buffer and subjecting the cells to a high-voltage electric pulse (e.g., by electroporation). A further method for introducing naked DNA cells is by mixing the DNA with a liposome suspension containing cationic lipids. The DNA/liposome complex is then incubated with cells. Naked DNA can also be directly injected into cells by, for example, microinjection.

Alternatively, naked DNA can also be introduced into cells by complexing the DNA to a cation, such as polylysine, which is coupled to a ligand for a cell-surface receptor (see for example Wu, G. and Wu, C. H. J. Biol. Chem. 263: 14621, 1988; Wilson et al. J. Biol. Chem. 267:963-967, 1992; and U.S. Pat. No. 5,166,320, each of which is hereby incorporated by reference in its entirety). Binding of the DNA-ligand complex to the receptor facilitates uptake of the DNA by receptor-mediated endocytosis.

Use of viral vectors containing particular nucleic acid sequences, e.g., a cDNA encoding a protein, is a common approach for introducing nucleic acid sequences into a cell. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are generally expressed efficiently in cells that have taken up viral vector nucleic acid.

Defective retroviruses are well characterized for use in gene transfer for gene therapy purposes (for a review see Miller, A. D. Blood 76:271, 1990). A recombinant retrovirus can be constructed having a nucleic acid encoding a protein of interest inserted into the retroviral genome. Additionally, portions of the retroviral genome can be removed to render the retrovirus replication defective. Such a replication defective retrovirus is then packaged into virions which can be used to infect a target cell through the use of a helper virus by standard techniques.

The genome of an adenovirus can be manipulated such that it encodes and expresses a protein of interest but is inactivated in terms of its ability to replicate in a normal lytic viral life cycle. See, for example, Berkner et al. BioTechniques 6:616, 1988; Rosenfeld et al. Science 252:431-434, 1991; and Rosenfeld et al. Cell 68:143-155, 1992. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses are advantageous in that they do not require dividing cells to be effective gene delivery vehicles and can be used to infect a wide variety of cell types, including airway epithelium (Rosenfeld et al., 1992, cited supra), endothelial cells (Lemarchand et al., Proc. Natl. Acad. Sci. USA 89:6482-6486, 1992), hepatocytes (Herz and Gerard, Proc. Natl. Acad. Sci. USA 90:2812-2816, 1993) and muscle cells (Quantin et al., Proc. Natl. Acad. Sci. USA 89:2581-2584, 1992). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham, J. Virol. 57:267, 1986). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol., 158:97-129, 1992). It is also one of the few viruses that may integrate its DNA into non-dividing cells, and exhibits a high frequency of stable integration (see for example Flotte et al., Am. J. Respir. Cell. Mol. Biol. 7:349-356, 1992; Samulski et al., J. Virol. 63:3822-3828, 1989; and McLaughlin et al., J. Virol. 62:1963-1973, 1989). Vectors containing as little as 300 base pairs of AAV can be packaged and can integrate. Space for exogenous DNA is limited to about 4.5 kb. An AAV vector such as that described in Tratschin et al. (Mol. Cell. Biol. 5:3251-3260, 1985) can be used to introduce DNA into cells. A variety of nucleic acids have been introduced into different cell types using AAV vectors (see for example Hermonat et al., Proc. Natl. Acad. Sci. USA 81:6466-6470, 1984; Tratschin et al., Mol. Cell. Biol. 4:2072-2081, 1985; Wondisford et al., Mol. Endocrinol. 2:32-39, 1988; Tratschin et al., J. Virol. 51:611-619, 1984; and Flotte et al., J. Biol. Chem. 268:3781-3790, 1993).

When the method used to introduce nucleic acid molecules into a population of cells results in modification of a large proportion of the cells and efficient expression of the protein by the cells, the modified population of cells may be used without further isolation or subcloning of individual cells within the population. That is, there may be sufficient production of the protein by the population of cells such that no further cell isolation is needed and the population can be immediately be used to seed a cell culture for the production of the protein. Alternatively, it may be desirable to isolate and expand a homogenous population of cells from a few cells or a single cell that efficiently produce(s) the protein.

A gene encoding a protein of interest may optionally be linked to one or more regulatory genetic control elements. In certain embodiments, a genetic control element directs constitutive expression of the protein. In certain embodiments, a genetic control element that provides inducible expression of a gene encoding the protein of interest can be used. The use of an inducible genetic control element (e.g., an inducible promoter) allows for modulation of the production of the protein in the cell. Non-limiting examples of potentially useful inducible genetic control elements for use in eukaryotic cells include hormone-regulated elements (e.g., see Mader, S. and White, J. H., *Proc. Natl. Acad. Sci. USA* 90:5603-5607, 1993), synthetic ligand-regulated elements (see, e.g. Spencer, D. M. et al., *Science* 262:1019-1024, 1993) and ionizing radiation-regulated elements (e.g., see Manome, Y. et al., *Biochemistry* 32:10607-10613, 1993; Datta, R. et al., *Proc. Natl. Acad. Sci. USA* 89:10149-10153, 1992). Additional cell-specific or other regulatory systems known in the art may be used in accordance with the invention.

One of ordinary skill in the art will be able to choose and, optionally, to appropriately modify the method of introducing genes that cause the cell to express the protein of interest in accordance with the teachings of the present invention.

Immunogenic Compositions

The RSV F proteins of subtype A and B produced by the methods disclosed herein can be included in immunogenic compositions for use as vaccines.

In addition to the immunogenic component, the vaccine may further comprise an immunomodulatory agent, such as an adjuvant. Examples of suitable adjuvants include aluminum salts such as aluminum hydroxide and/or aluminum phosphate; oil-emulsion compositions (or oil-in-water compositions), including squalene-water emulsions, such as MF59 (see e.g., WO 90/14837); saponin formulations, such as, for example, QS21 and Immunostimulating Complexes (ISCOMS) (see e.g., U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like. It is also possible to use vector-encoded adjuvant, e.g., by using heterologous nucleic acid that encodes a fusion of the oligomerization domain of C4-binding protein (C4 bp) to the antigen of interest (e.g., Solabomi et al., 2008, Infect Immun 76: 3817-23). In certain embodiments the compositions hereof comprise aluminum as an adjuvant, e.g., in the form of aluminum hydroxide, aluminum phosphate, aluminum potassium phosphate, or combinations thereof, in concentrations of 0.05-5 mg, e.g., from 0.075-1.0 mg, of aluminum content per dose.

EXAMPLES

GS-CHO clones recombinantly expressing RSV F protein of subtype A (hereafter RSV F (A)) or of subtype B (hereafter RSV F (B)) were maintained at 36.5° C. and 5% $CO_2$ in a 120 or 140 rpm shaking incubator. Cultures were seeded at $0.35\times10^6$ cells/mL or $0.20\times10^6$ cells/mL for 3 or 4 day passages during seed expansion, respectively. The N−1 seed cultures for all experiments were run in 2 L Applikon® bioreactors with 1 L working volume and passaged at $0.70\times10^6$ cells/mL for 4 days in a medium with high nutrient content.

Production experiments were performed in 2 L Applikon® bioreactors with BioNet® controllers using a glucose restricted fed-batch process, hereafter referred to as a HiPDOG process (Gagnon et al (2011) Biotechnology and bioengineering 108: 1328-1337). Specific methods and parameters are listed in the subsequent experiment sections.

On the day of harvest, the cell culture broth is clarified by centrifugation and depth filtration. Downstream processing includes ultrafiltration and diafiltration 1 (UF/DF1), to concentrate and buffer exchange material prior to the capture chromatography step, an anion exchange chromatography (AEX) column, operated in bind and elute mode. The polishing columns include a ceramic hydroxyapatite chromatography (CHA) in flow through mode and hydrophobic interaction chromatography (HIC) column in bind and elute mode. The downstream process concludes with a virus retaining filtration step, an ultrafiltration and diafiltration 2 (UF/DF2), and a final filtration step.

In the following experiments, titer, trimer, high molecular mass species (HMMS), low molecular mass species (LMMS) and host cell protein (HCP) are reported.

Titer can be determined by any method known in the art. In the following experiment, titer was measured by reverse phase high-performance liquid chromatography (RP-HPLC). Reversed phase chromatography separates molecules based on polarity. Relatively non-polar molecules, including RSV F protein of subtype A or B, bind to the column, while polar molecules flow through the column without binding. The bound molecules are eluted from the column through the application of a mobile phase gradient that passes from polar to less polar conditions. Molecules are eluted in order of decreasing polarity. Detection is performed using ultraviolet (UV) absorption at 220 nm. Titer determination is accomplished through comparison of sample peak area to that of a calibration standard.

The following conditions were used in the following experiments disclosed herein:

| Condition | Setting |
|---|---|
| Column Type | Agilent Zorbax, 300SB-C3, 150 × 3.0 mm, 3.5 μm |
| Mobile Phase A (MPA) | 0.1% TFA (v/v) in water |
| Mobile Phase B (MPB) | 0.1% TFA (v/v) in 90% acetonitrile |
| Column Temperature | 55 ± 5° C. |
| Flow Rate & Run Time | 0.75 mL/minute for 20 minutes |
| Autosampler Temperature | 5 ± 3° C. |
| Injection Volume | 5-100 μL (15 μg target load) |
| Detector Wavelength | UV at 220 nm |

Gradient Conditions

| Time (minutes) | Flow Rate (mL/min) | % MPA | % MPB |
|---|---|---|---|
| 0 | 0.75 | 90 | 10 |
| 2 | 0.75 | 90 | 10 |
| 2.1 | 0.75 | 65 | 35 |
| 12 | 0.75 | 27 | 73 |
| 12.1 | 0.75 | 5 | 95 |
| 16 | 0.75 | 5 | 95 |
| 16.1 | 0.75 | 90 | 10 |
| 20 | 0.75 | 90 | 10 |

Trimer, HMMS and LMMS were measured by size exclusion chromatography (SEC-HPLC). SEC-HPLC is an analytical method known to the skilled person and used to determine the relative content of high molecular mass species (HMMS), trimer and low molecular mass species (LMMS) in the RSV F protein of subtype A or B samples obtained by the methods of the invention. SEC-HPLC separates molecules by their hydrodynamic volume. When the analyte is applied to the head of the column bed, molecules that are smaller than the pores of the packing material can diffuse into and out of the pores, whereas those that are larger do not enter the pores. As a result, the larger molecules pass through the column more quickly and smaller molecules more slowly. Once the species elute, they are detected by UV absorption at 280 nm. Low Molecular Mass species (LMMS) is the term used for all species of apparent molecular mass less than the trimer as measured by SEC-HPLC. They elute after the trimer peak. High Molecular Mass species (HMMS) is the term used for all peaks of apparent molecular mass greater than the trimer as measured by SEC-HPLC. They elute before the trimer peak and may include aggregates.

HCP was measured by enzyme-linked immunoassay (ELISA), a quantitative assay which measures residual Chinese Hamster Ovary (CHO) Host Cell Proteins (HCPs), using a sandwich-type ELISA analysis. The major steps in the HCP assay are outlined below.

A set of standard samples are prepared from highly enriched CHO HCP material. The standard samples range in concentration from 2 ng/mL to 256 ng/mL of CHO HCPs. Test samples are diluted to four RSV protein F of subtype A or B concentrations. Lastly, a control sample is tested on each assay plate. The assay plate is coated with polyclonal antibodies raised against the highly enriched preparation of the CHO HCPs (anti-CHO HCPP pAbs). After the coating is completed, the plate is blocked to minimize non-specific binding of analytes and reagents. After blocking, the standards, the test samples, and the control sample are added to the assay plate and incubated to allow the HCPs in these samples to be captured by the anti-CHO HCP antibodies. The plate is then washed to remove any unbound proteins and leave the HCP-antibody complex. To quantify the amount of bound HCPs in each well, a preparation of the anti-CHO HCP antibody conjugated to biotin is added to the assay plate and allowed to bind to the captured HCPs. The plate is washed to remove any unbound biotinylated antibody and a streptavidin-horseradish peroxidase (HRP) conjugate is added which binds to the biotin-anti-CHO HCP conjugate. The plate is washed to remove any unbound streptavidin-HRP and a solution of 3,3',5,5'-tetramethyl benzidine (TMB) is added to the assay plate. TMB is a substrate which generates a blue color in the presence of HRP. The assay plates are incubated with the TMB reagent for a period of time to generate an appropriate signal in each of the wells and the peroxidase reaction is quenched by the addition of sulfuric acid. Lastly the absorbance in each well is measured and recorded at 450 nm using a suitable plate reader. The generated signal is proportional to the amount of HCPs captured on the assay plate. The signal in the standard sample wells is plotted against the standard HCP concentration. The plot is fit to a four-parameter logistic (4PL) fit to generate an HCP standard curve. The signal in the test samples and the external control sample is then used to determine the HCP content in these samples by interpolation of the absorbance signal against the pseudo linear portion of the standard 4PL function.

From an overall productivity and downstream filterability perspective, the process is most optimal when titer and trimer are maximized and HMMS, LMMS and HCP are minimized. RP-HPLC titer measures the total amount of RSV protein present in the sample, including aggregate and RSV protein that is not in the trimeric form. Trimer, as measured by SEC, provides an estimate of approximately how much RSV molecule in the trimeric form is present as a percentage of the total amount of protein present (including some process impurities). The manipulation of process parameters, such as growth temperature, may increase trimer while negatively impacting titer (or vice versa). To demonstrate the overall impact to both titer and trimer, "triter" is reported, which is calculated by multiplying trimer by titer. Triter provides an estimate of how much protein is produced in the trimeric form.

Example 1—Effect of Temperature on RSV F Protein Production in CHO Cells

This set of experiments was designed to assess the effect of the temperature pre and post shift as well as the timing of the shift on titer and trimer formation during the production of RSV F proteins of subtype A and B by CHO cells.

Production experiments were performed in 2 L Applikon® bioreactors with BioNet® controllers using conditions detailed in Table 1. All conditions were run in a fedbatch process comprising a phase where the amount of glucose provided to the cells is restricted (HipDOG from day 0 to day 5 for RSV F (A) and day 0 to day 4 for RSV F (B)) and using a cell culture medium without hydrocortisone.

TABLE 1

| Bioreactor Production Process Parameters | |
|---|---|
| Inoculation Density | $3.0 \times 10^6$ cells/mL |
| Process | Fed batch with HiPDOG |
| pH set point during HiPDOG | 7.075 +/− 0.025 |
| pH set point post HiPDOG | 7.05 +/− 0.15 |
| DO set point | 40% |
| Agitation | 80 W/m$^3$ |
| Impellers | Rushton (1) |
| Sparger | 100 μm sintered steel |
| Sparge | Pure $O_2$ |
| Headspace | Air/7% $CO_2$ mix @ 100 sccm |
| Feed Rate Post HiPDOG | RSV F subtype A: 21 mL/L/day<br>RSV F subtype B: 25.5 mL/L/day |
| Glucose Feed | 500 g/L glucose, target 2 g/L |
| Titrant | 0.94M sodium carbonate + 0.06M potassium carbonate |
| Antifoam | EX-CELL ® as needed |
| Process Duration | 12 days |
| Vessel Size | 2 L Applikon ® |
| Working Volume | 1 L |

1.1 Effect of Growth Temperature

In this experiment, the cells were grown at a temperature of 33° C., 34.5° C. or 36° C. to assess the effect of the growth temperature on titer, percentage of trimer, HMMS, LMMS, triter and the amount of Host Cell Protein (HOP). The results are shown in Table 2 and in FIGS. 1A, SB, 2A, 2B, 3A, 3B, 4A and 4B.

TABLE 2

Effect of growth temperature

| Cell line | Growth Temp. (° C.) | Production Temp. (° C.) | Temp. Shift (hours) | HCP (μg/mL) | RP-HPLC (g/L) | SEC HMMS (%) | SEC LMMS (%) | SEC Trimer (%) | Triter (g/L) |
|---|---|---|---|---|---|---|---|---|---|
| RSV F (A) | 33 | 31 | 144 | 242 | 0.62 | 32 | 24 | 44 | 0.27 |
| | 34.5 | 31 | 144 | 267 | 0.73 | 39 | 23 | 37 | 0.27 |
| | 36 | 31 | 144 | 307 | 0.63 | 45 | 25 | 30 | 0.19 |
| RSV F (B) | 33 | 31 | 144 | 131 | 1.44 | 33 | 12 | 55 | 0.78 |
| | 34.5 | 31 | 144 | 130 | 1.91 | 38 | 19 | 43 | 0.82 |
| | 36 | 31 | 144 | 243 | 1.74 | 42 | 21 | 37 | 0.64 |

Figure 2A:
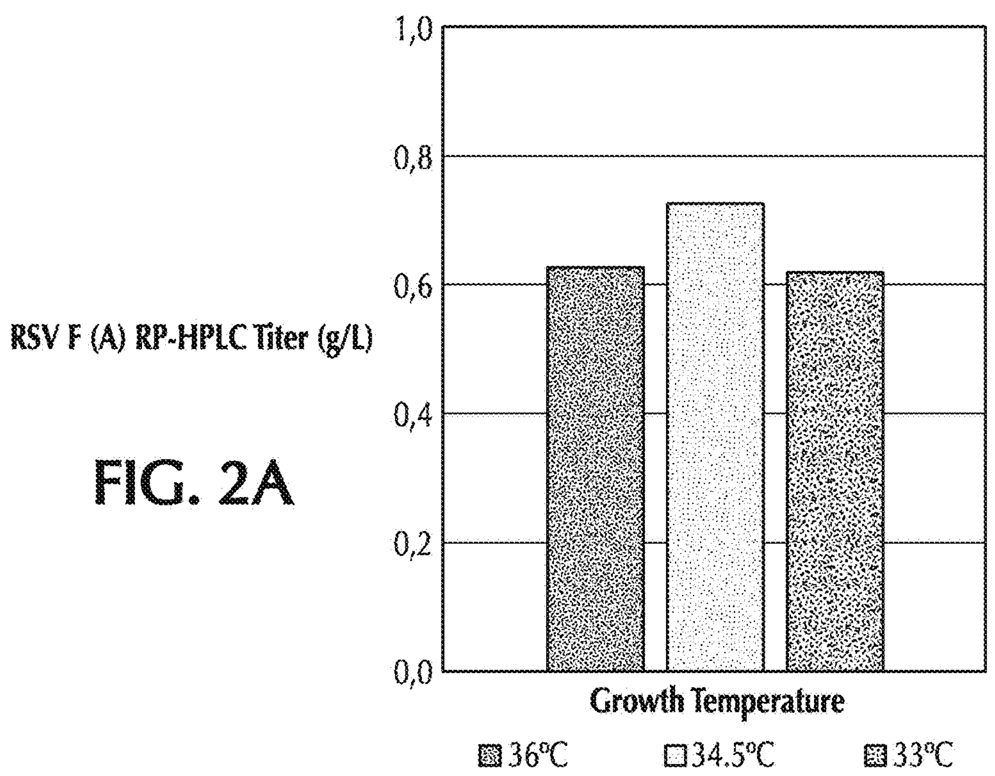
FIG. 2A shows the effect of the growth temperature on the titer of RSV F protein of subtype A as measured by RP-HPLC.
Figure 2B:
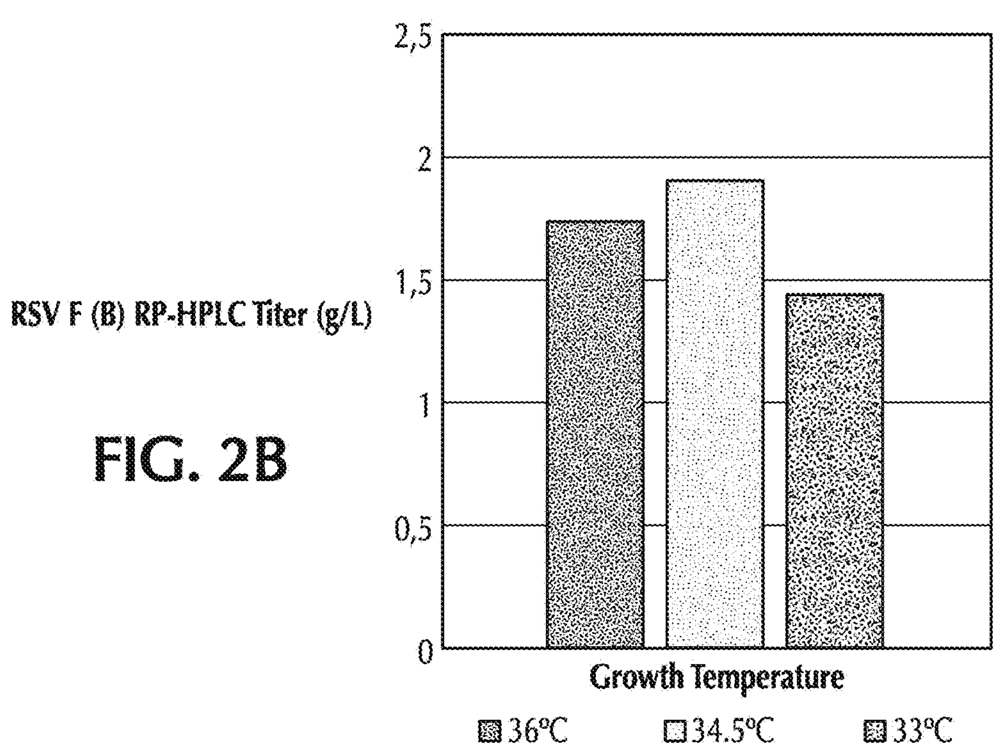
FIG. 2B shows the effect of the growth temperature on the titer of RSV F protein of subtype B as measured by RP-HPLC.

For both antigens, the growth temperature negatively correlated with percentage of trimer and positively correlated with percentage of HMMS and LMMS (see FIGS. 1A and AB). The highest titer was consistently obtained with the temperature of 34.5° C. (see FIGS. 2A and 21B).

Figure 3A:
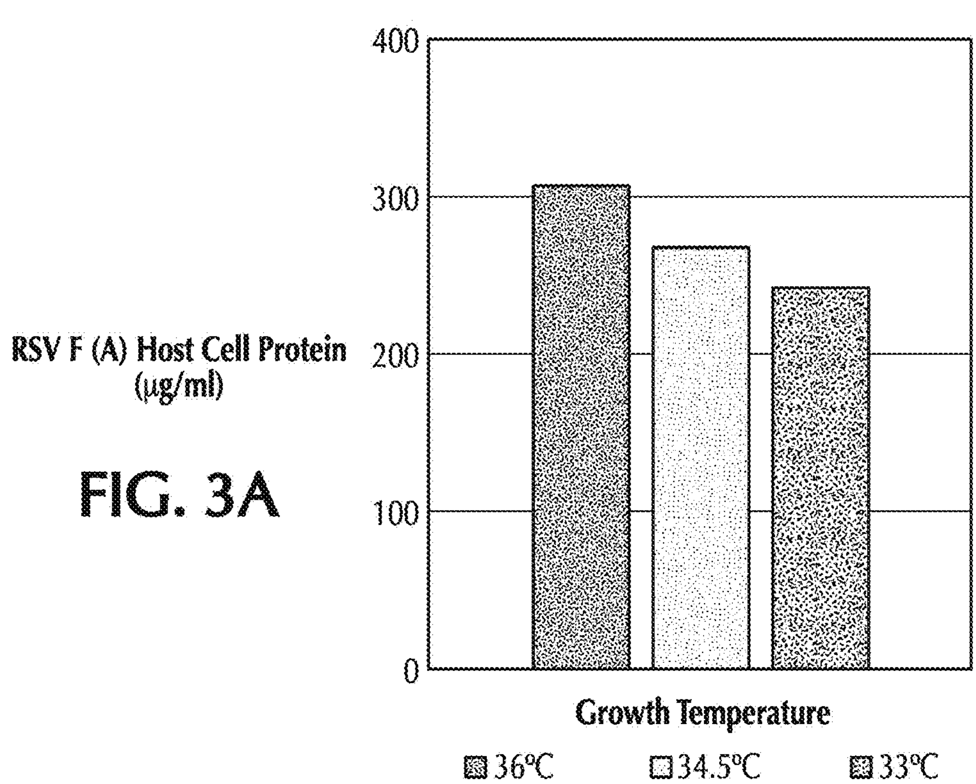
FIG. 3A shows the effect of the growth temperature on the amount of host cell protein (HCP) as measured by enzyme-linked immunoassay in material harvested from production of RSV F protein of subtype A.
Figure 3B:
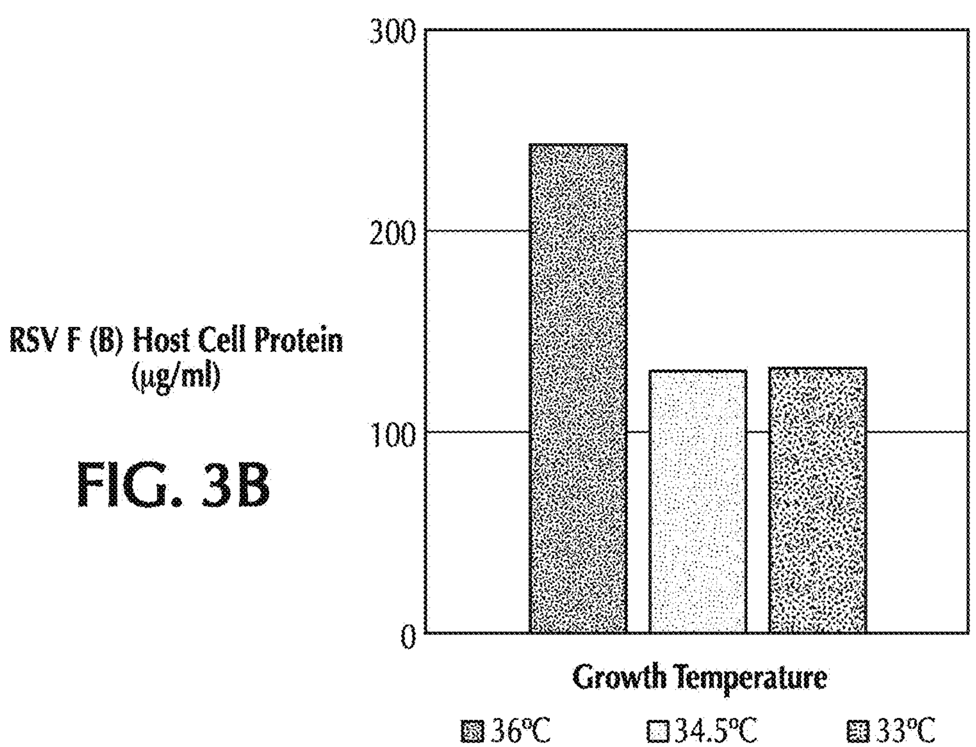
FIG. 3B shows the effect of the growth temperature on the amount of host cell protein (HCP) as measured by enzyme-linked immunoassay in material harvested from production of RSV F protein of subtype B.
Figure 4A:
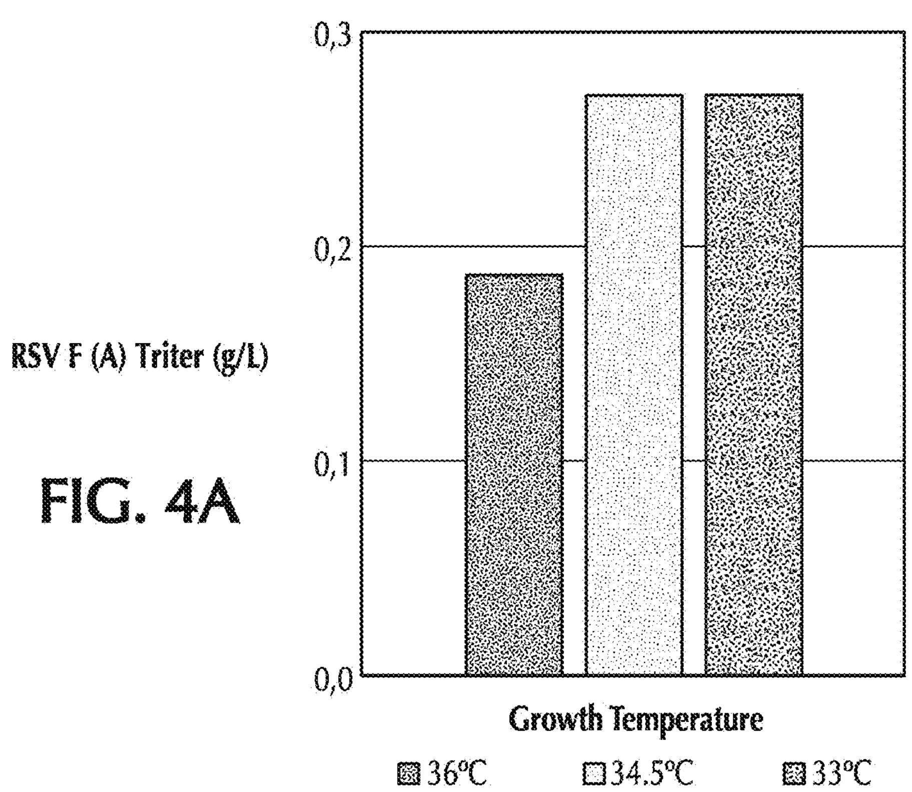
FIG. 4A shows the effect of the growth temperature on the amount of triter in material harvested from production of RSV F protein of subtype A.
Figure 4B:
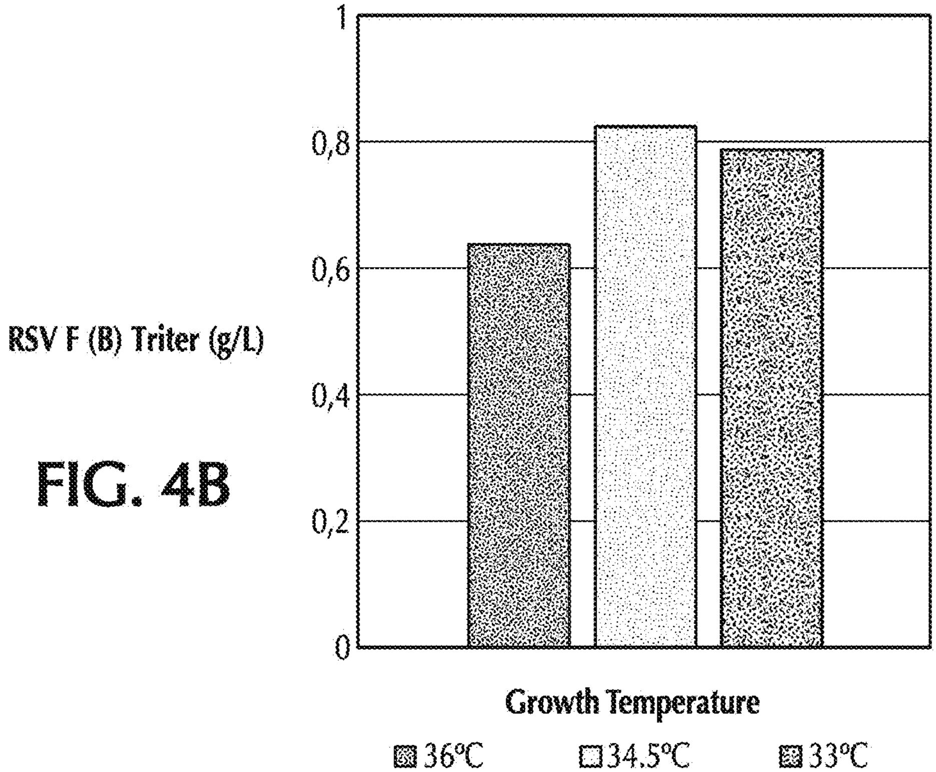
FIG. 4B shows the effect of the growth temperature on the amount of triter in material harvested from production of RSV F protein of subtype B.

A growth temperature between 34° C. and 35° C., and preferably 34.5° C. is suitable for maximizing trimer, titer and minimizing impurities. For both antigens, HCP levels positively correlated with temperature (see FIGS. 3A and 3B). For subtype B, the highest triter was obtained with the temperature of 34.5° C. and for subtype A the triter at 33° C. and 34.5° C. was higher than at 36° C. (see FIGS. 4A and 4B).

1.2 Effect of Production Temperature

In this experiment, the growth temperature was 34.5° C. and the production temperature was varied (28.5° C., 31° C. or 34° C.) to assess the effect of the production temperature on titer, percentage of trimer, HMMS, LMMS, triter, and the amount of HCP. The results are shown in Table 3 and in FIGS. 5A, 5B, 6A, 6B, 7A, 7B, 8A and 8B.

TABLE 3

Effect of production temperature

| Cell line | Growth Temp. (° C.) | Prod Temp. (° C.) | Temp. Shift (hrs) | HCP (μg/mL) | RP-HPLC (g/L) | SEC HMMS (%) | SEC LMMS (%) | SEC Trimer (%) | Triter (g/L) |
|---|---|---|---|---|---|---|---|---|---|
| RSV F (A) | 34.5 | 28.5 | 144 | 314 | 0.60 | 37 | 23 | 39 | 0.24 |
| | 34.5 | 31 | 144 | 267 | 0.73 | 39 | 23 | 37 | 0.27 |
| | 34.5 | 34 | 144 | 355 | 0.71 | 45 | 26 | 29 | 0.21 |
| RSV F (B) | 34.5 | 28.5 | 144 | 198 | 1.47 | 36 | 15 | 49 | 0.72 |
| | 34.5 | 31 | 144 | 130 | 1.91 | 38 | 19 | 43 | 0.82 |
| | 34.5 | 34 | 144 | 327 | 2.08 | 41 | 22 | 38 | 0.79 |

Figure 5A:
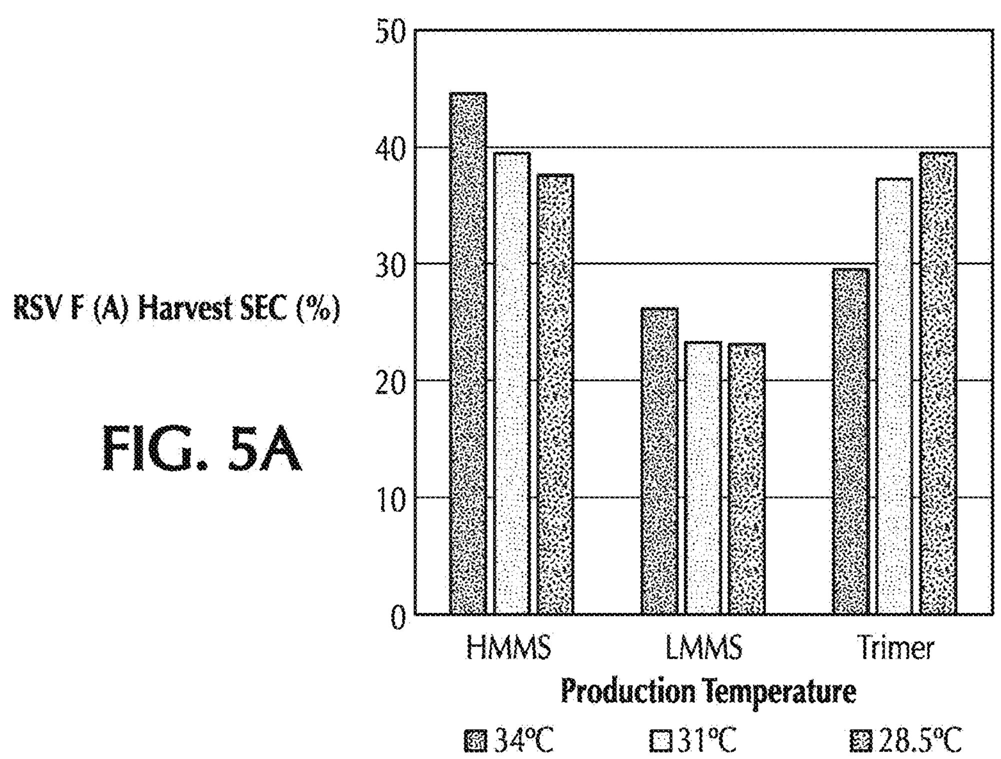
FIG. 5A shows the effect of the production temperature on the percentage of HMMS, LMMS and RSV F protein of subtype A trimer as measured by size exclusion chromatography.
Figure 5B:
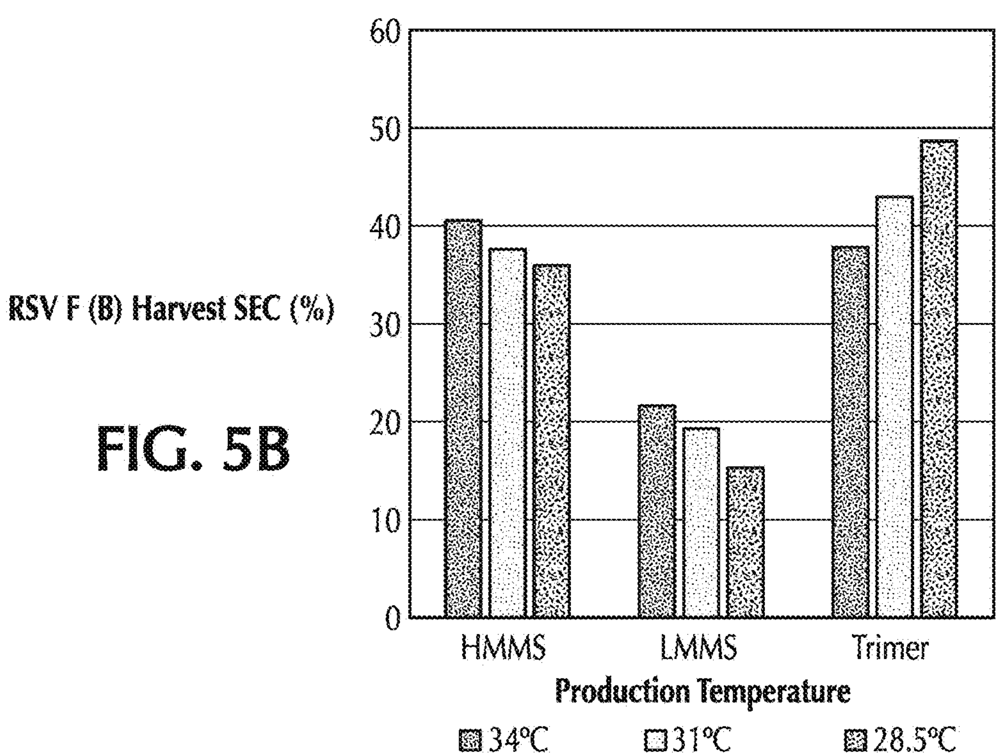
FIG. 5B shows the effect of the production temperature on the percentage of HMMS, LMMS and RSV F protein of subtype B trimer as measured by size exclusion chromatography
Figure 6A:
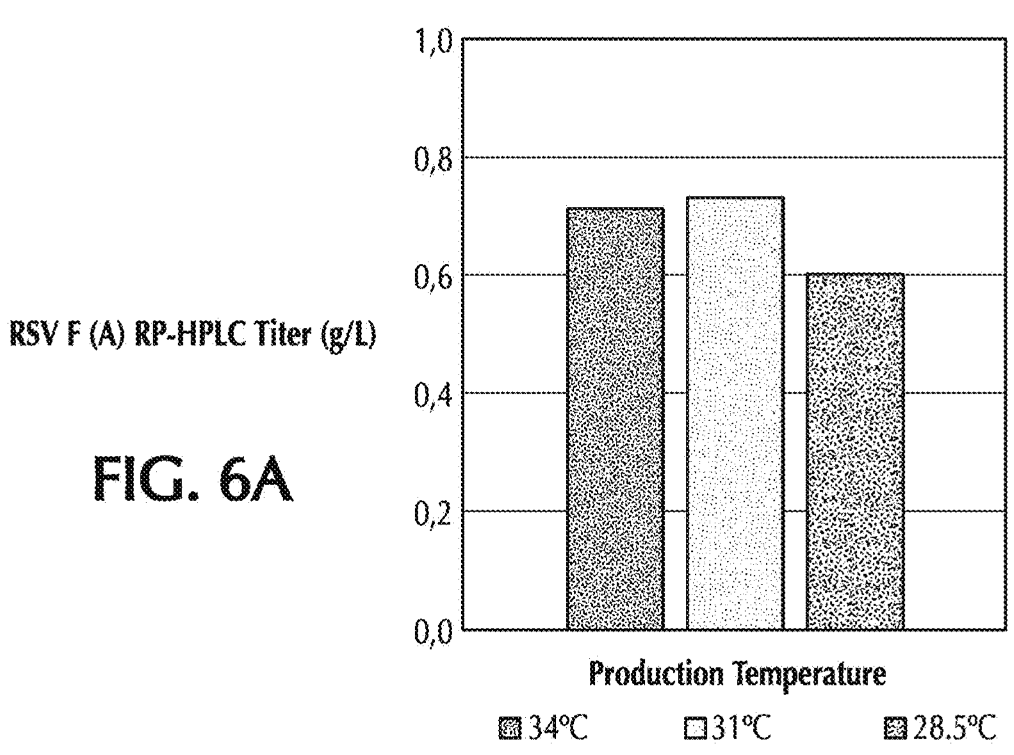
FIG. 6A shows the effect of the production temperature on the titer of RSV F protein of subtype A as measured by RP-HPLC.
Figure 6B:
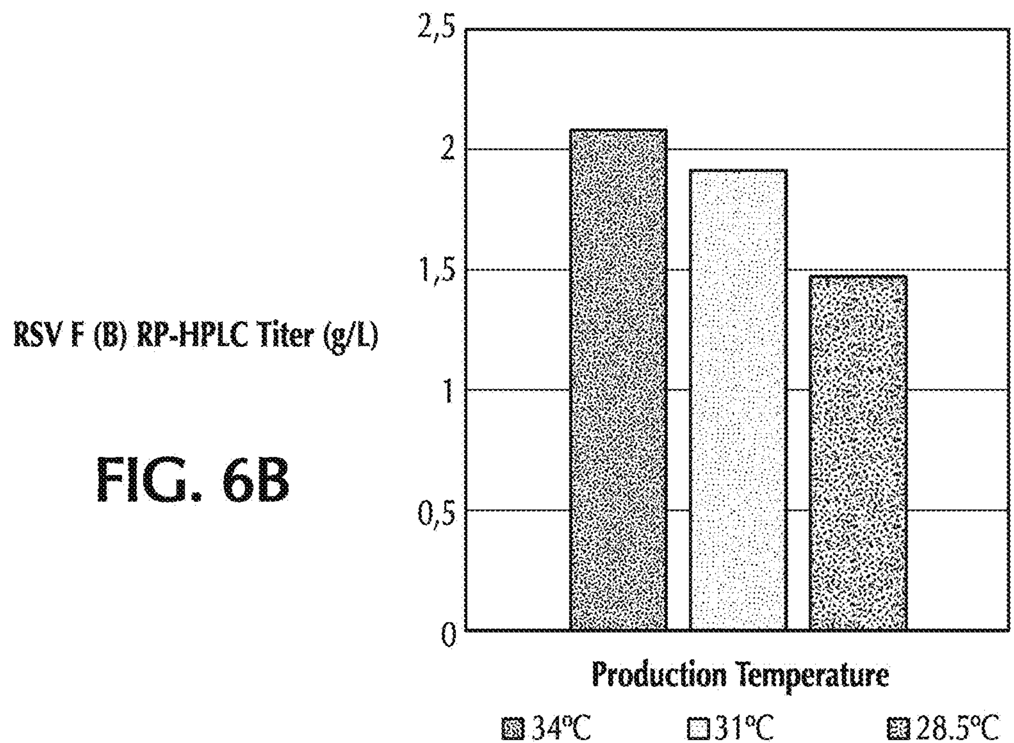
FIG. 6B shows the effect of the production temperature on the titer of RSV F protein of subtype B as measured by RP-HPLC.
Figure 7A:
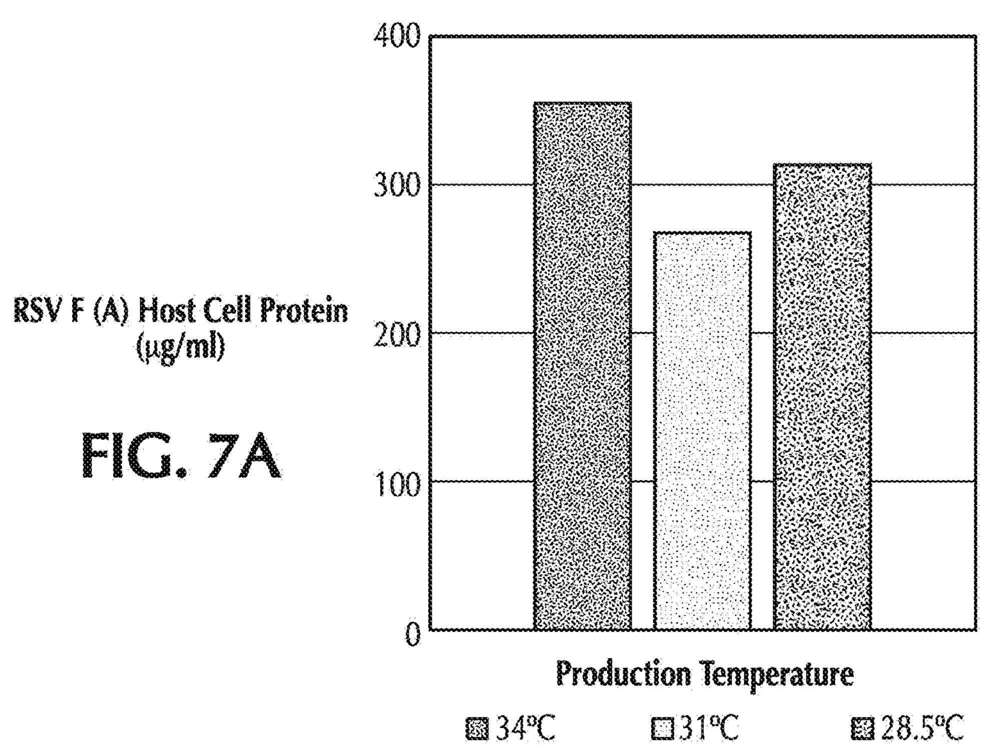
FIG. 7A shows the effect of the production temperature on the amount of host cell protein (HCP) as measured by enzyme-linked immunoassay in material harvested from production of RSV F protein of subtype A.
Figure 7B:
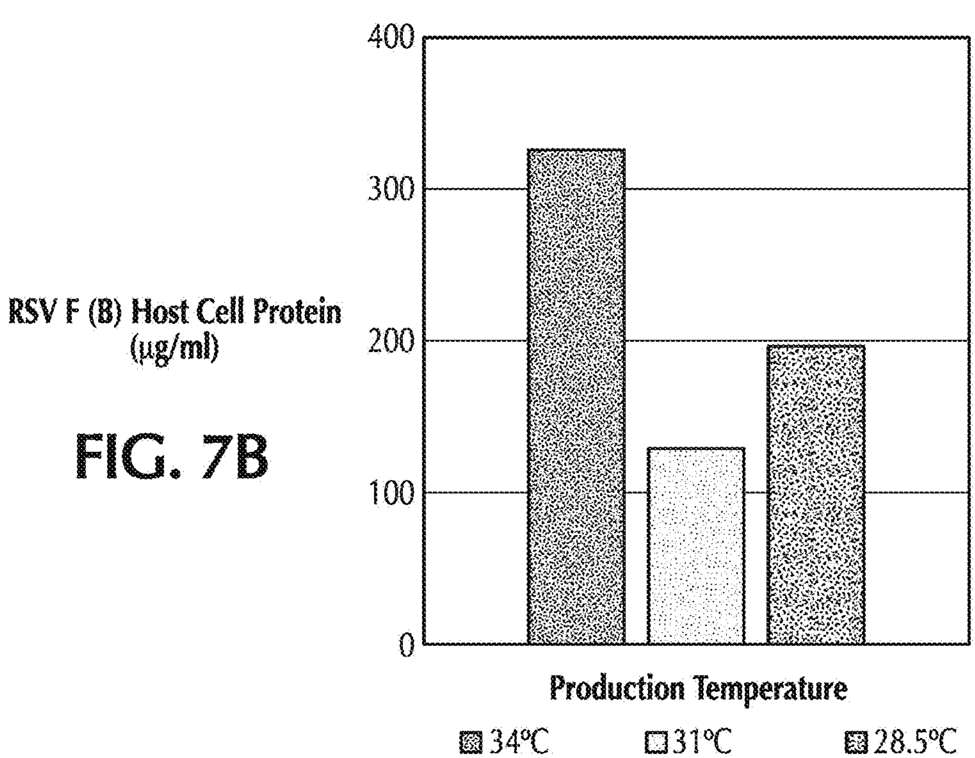
FIG. 7B shows the effect of the production temperature on the amount of host cell protein (HCP) as measured by enzyme-linked immunoassay in material harvested from production of RSV F protein of subtype B.
Figure 8A:
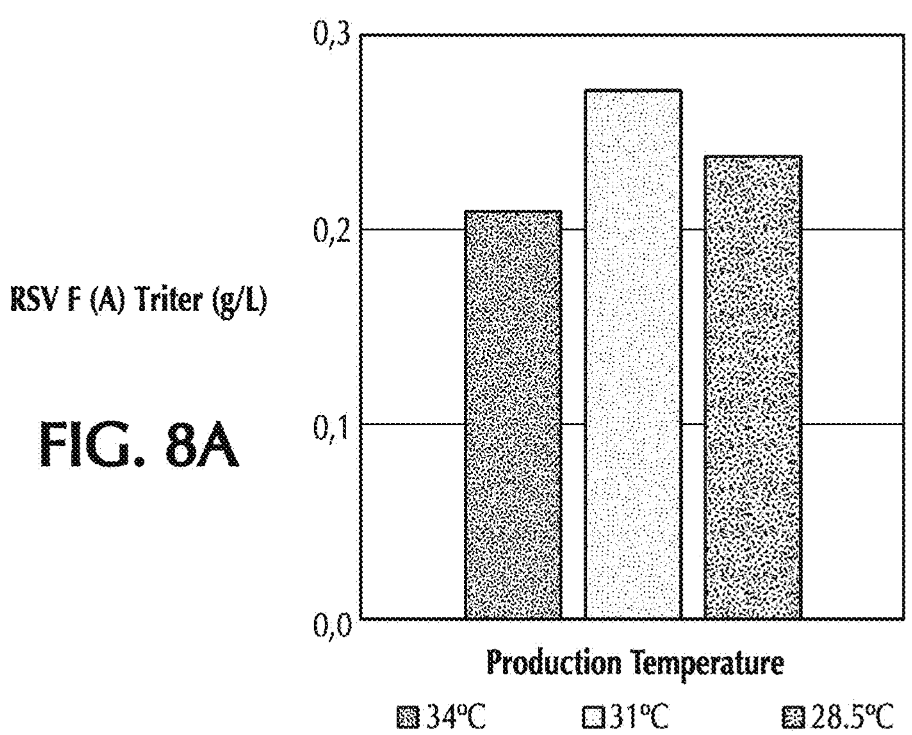
FIG. 8A shows the effect of the production temperature on the amount of triter in material harvested from production of RSV F protein of subtype A.
Figure 8B:
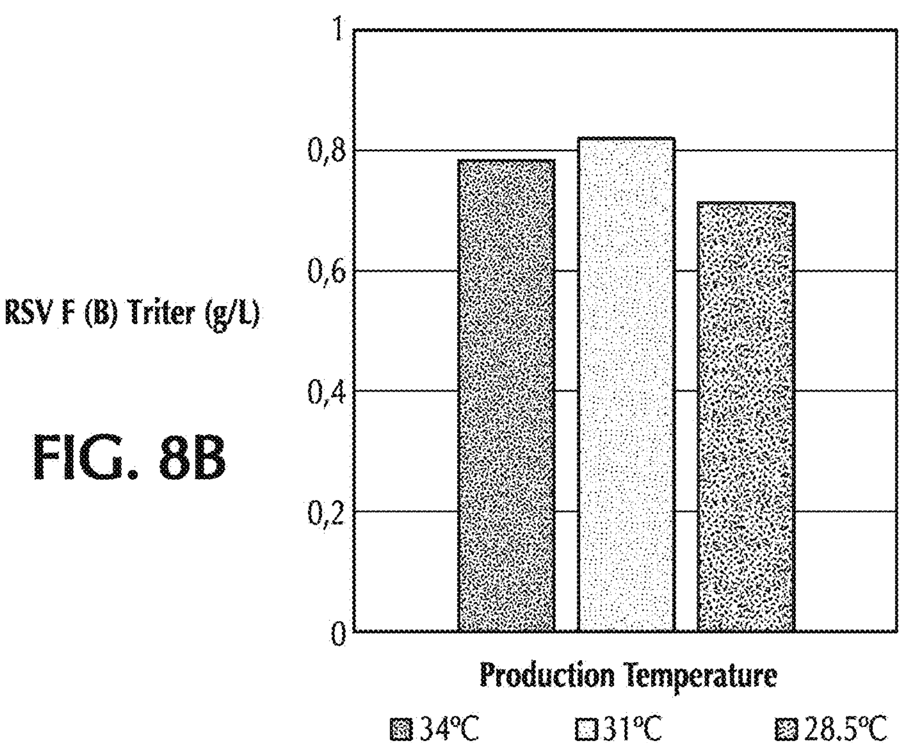
FIG. 8B shows the effect of the production temperature on the amount of triter in material harvested from production of RSV F protein of subtype B.
Figure 9A:
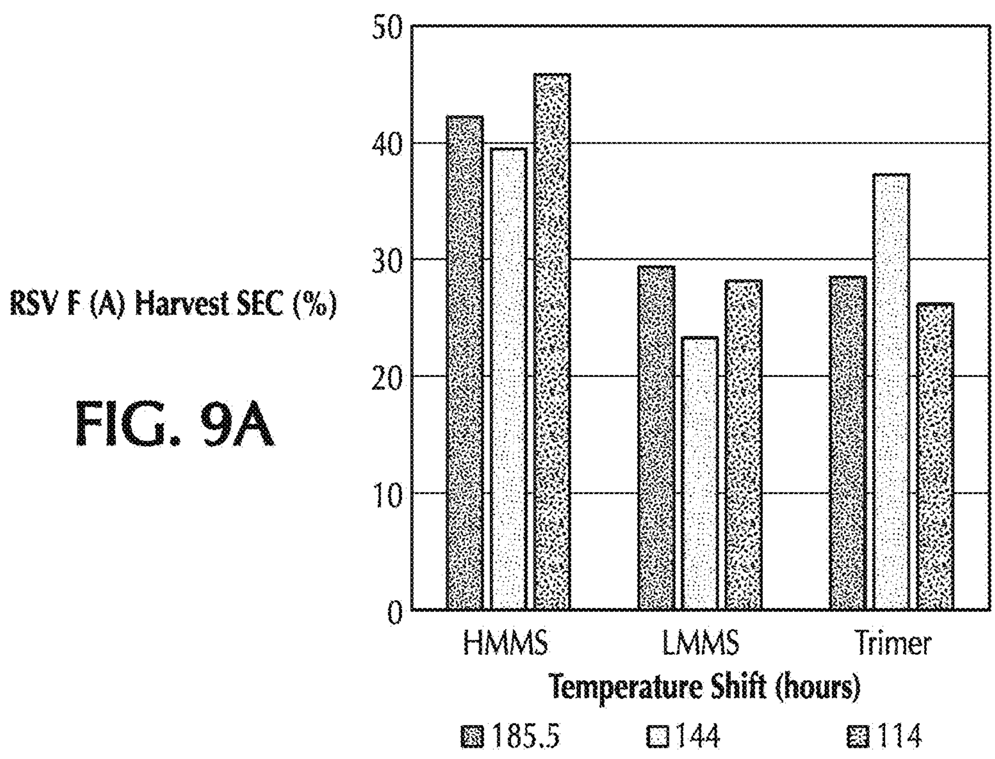
FIG. 9A shows the effect of the timing of a temperature shift on the percentage of HMMS, LMMS and RSV F protein of subtype A trimer as measured by size exclusion chromatography.
Figure 9B:
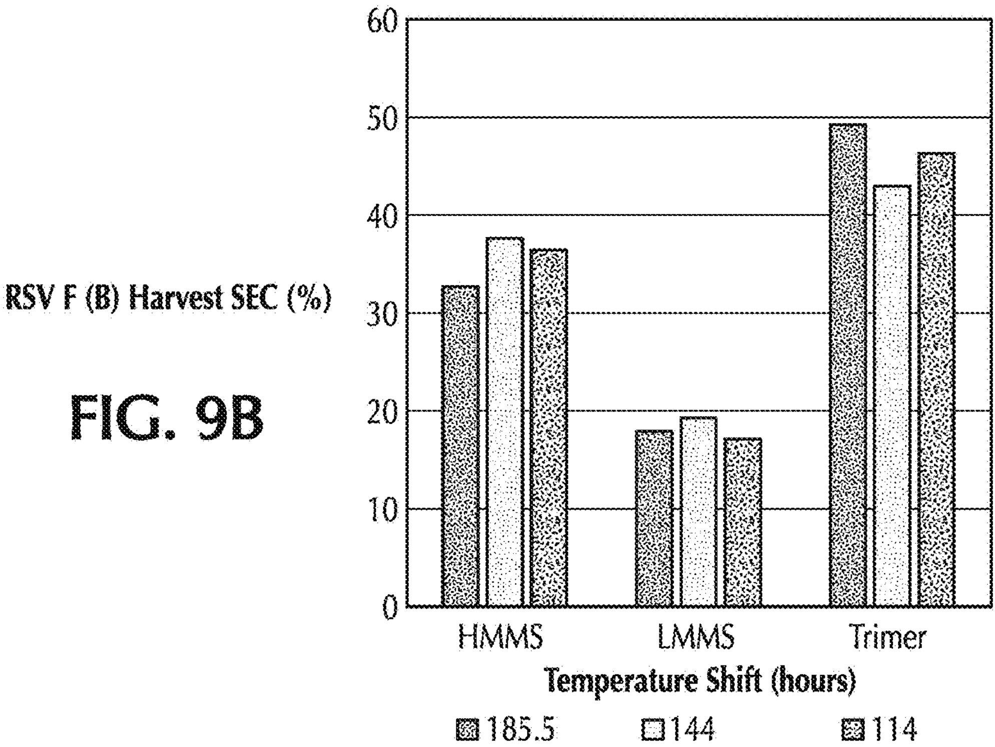
FIG. 9B shows the effect of the timing of a temperature shift on the percentage of HMMS, LMMS and RSV F protein of subtype B trimer as measured by size exclusion chromatography.
Figure 10A:
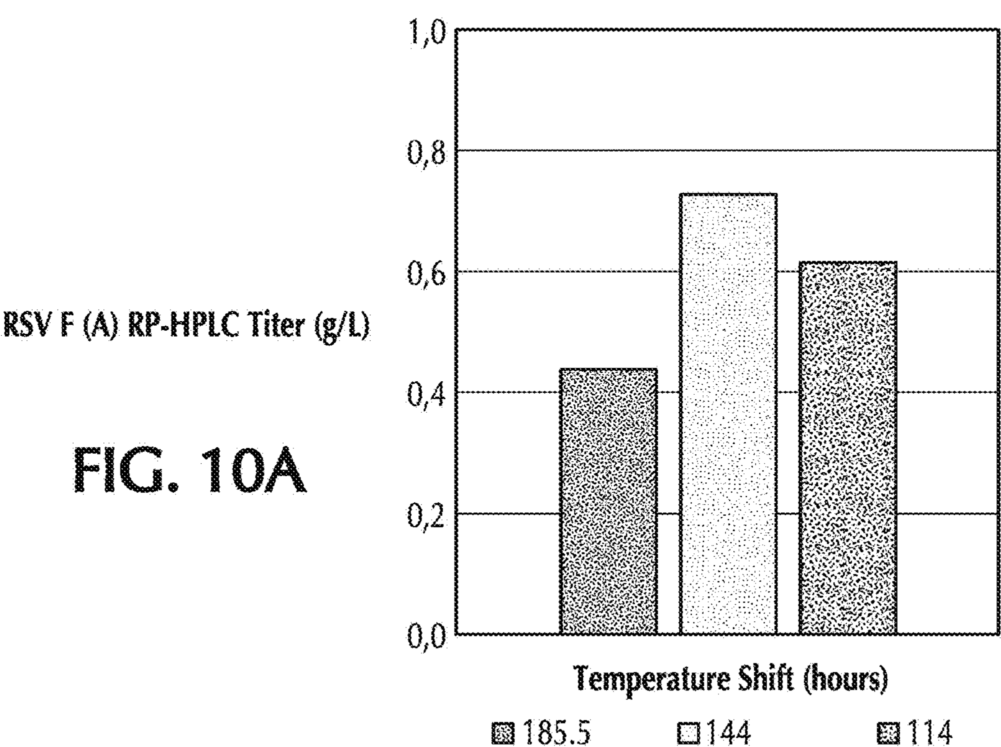
FIG. 10A shows the effect of the timing of a temperature shift on the titer of RSV F protein of subtype A as measured by RP-HPLC.
Figure 10B:
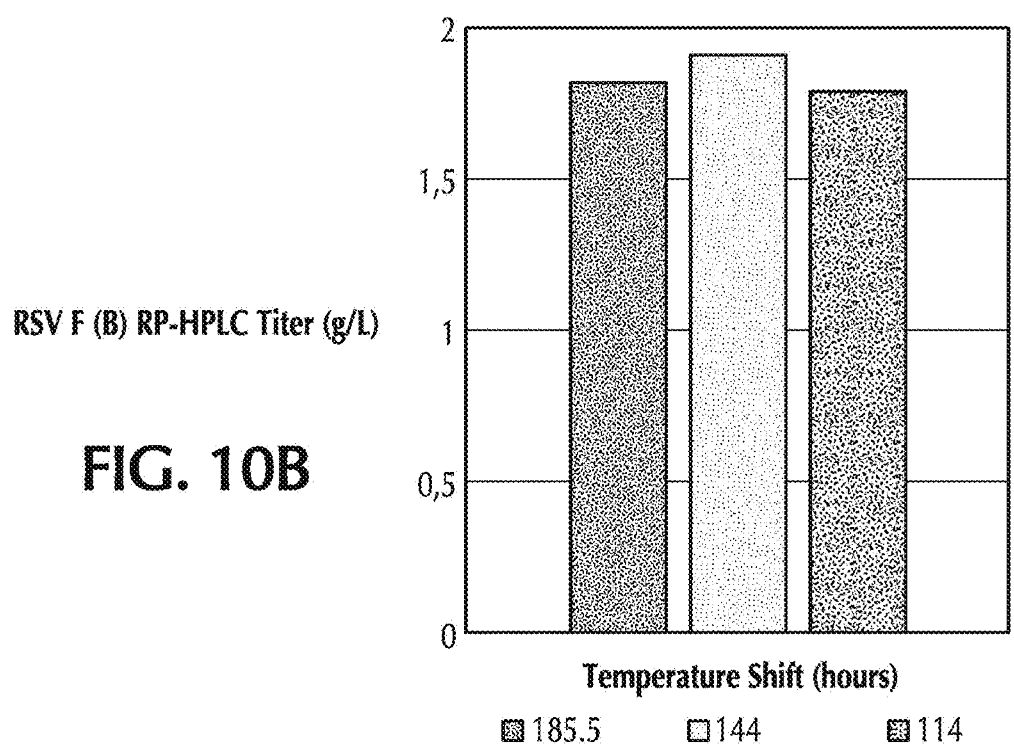
FIG. 10B shows the effect of the timing of a temperature shift on the titer of RSV F protein of subtype B as measured by RP-HPLC.
Figure 11A:
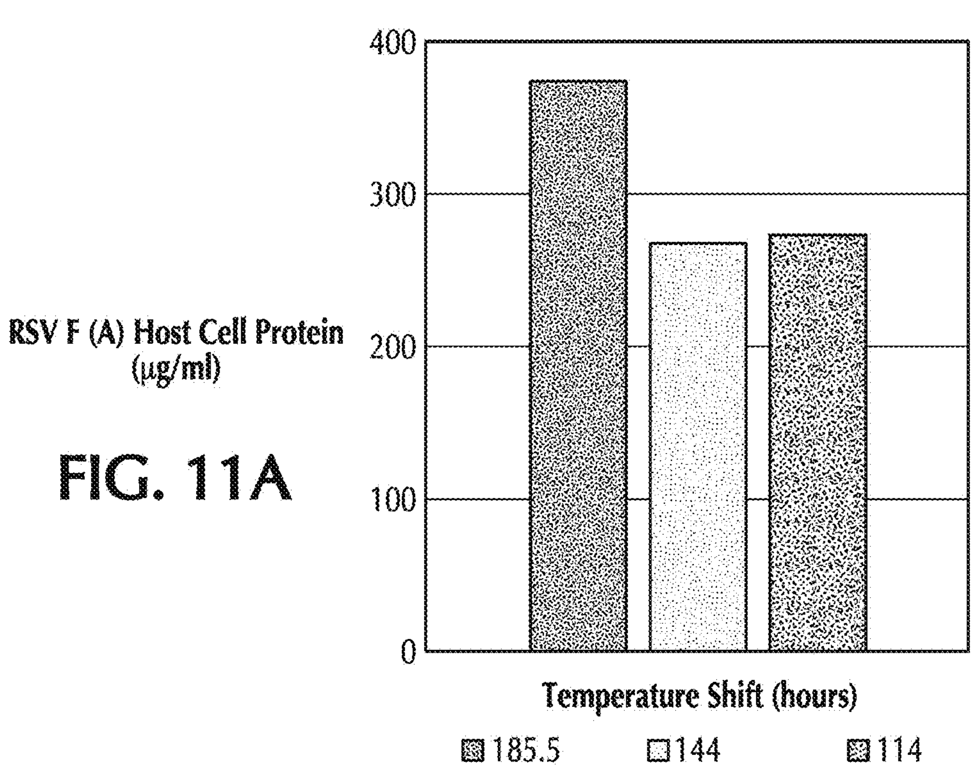
FIG. 11A shows the effect of the timing of a temperature shift on the amount of host cell protein (HCP) as measured by enzyme-linked immunoassay in material harvested from production of RSV F protein of subtype A.
Figure 11B:
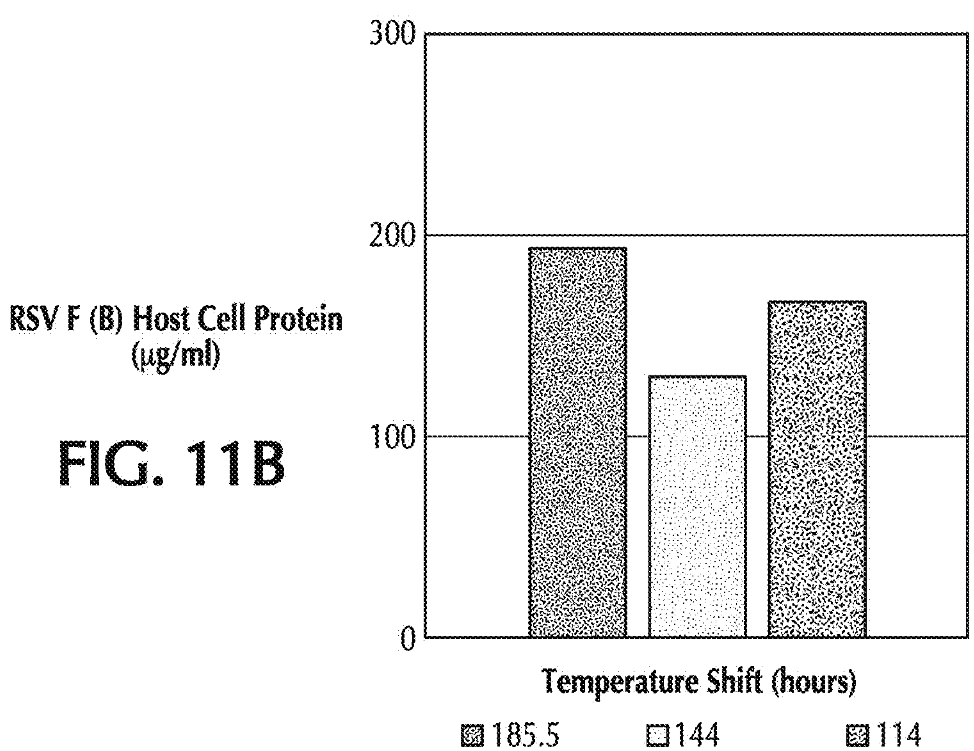
FIG. 11B shows the effect of the timing of a temperature shift on the amount of host cell protein (HCP) as measured by enzyme-linked immunoassay in material harvested from production of RSV F protein of subtype B.
Figure 12A:
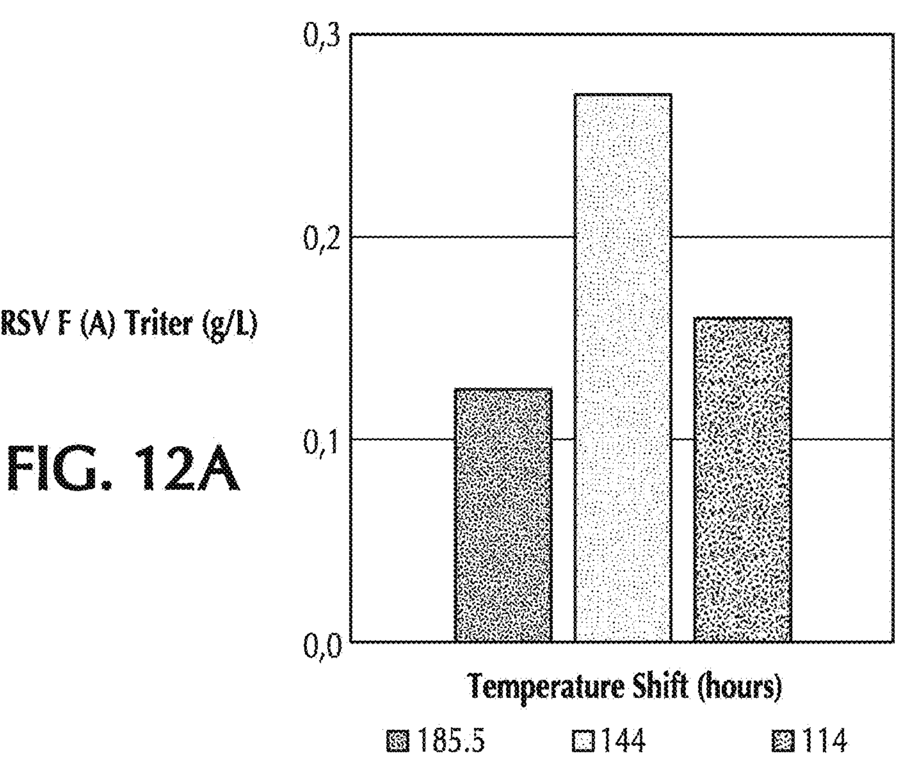
FIG. 12A shows the effect of the timing of a temperature shift on the amount of triter in material harvested from production of RSV F protein of subtype A.
Figure 12B:
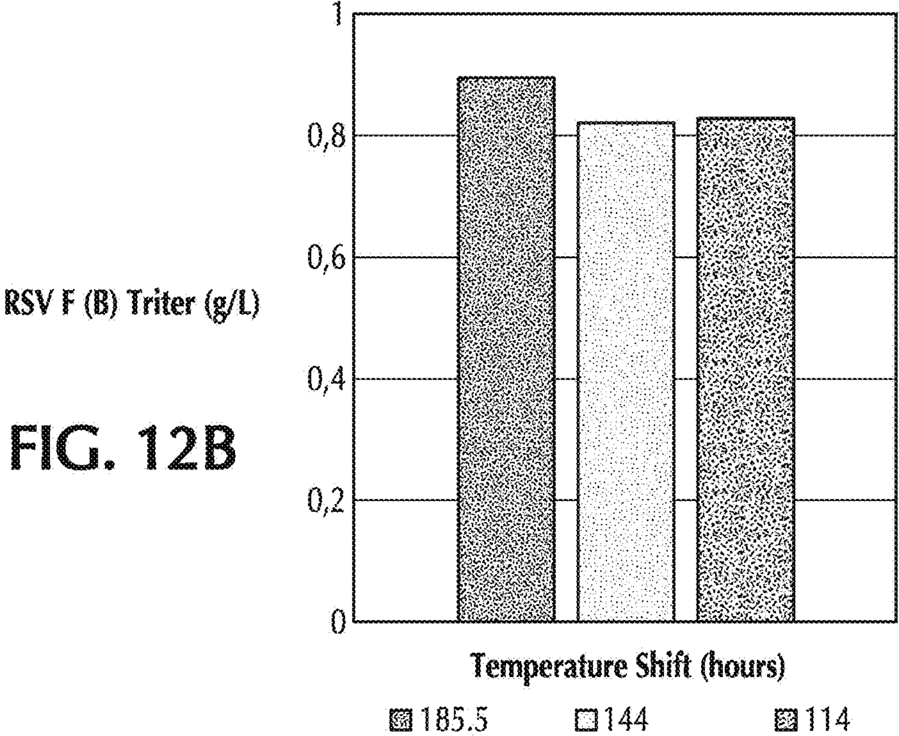
FIG. 12B shows the effect the timing of a temperature shift on the amount of triter in material harvested from production of RSV F protein of subtype B.
Figure 13A:
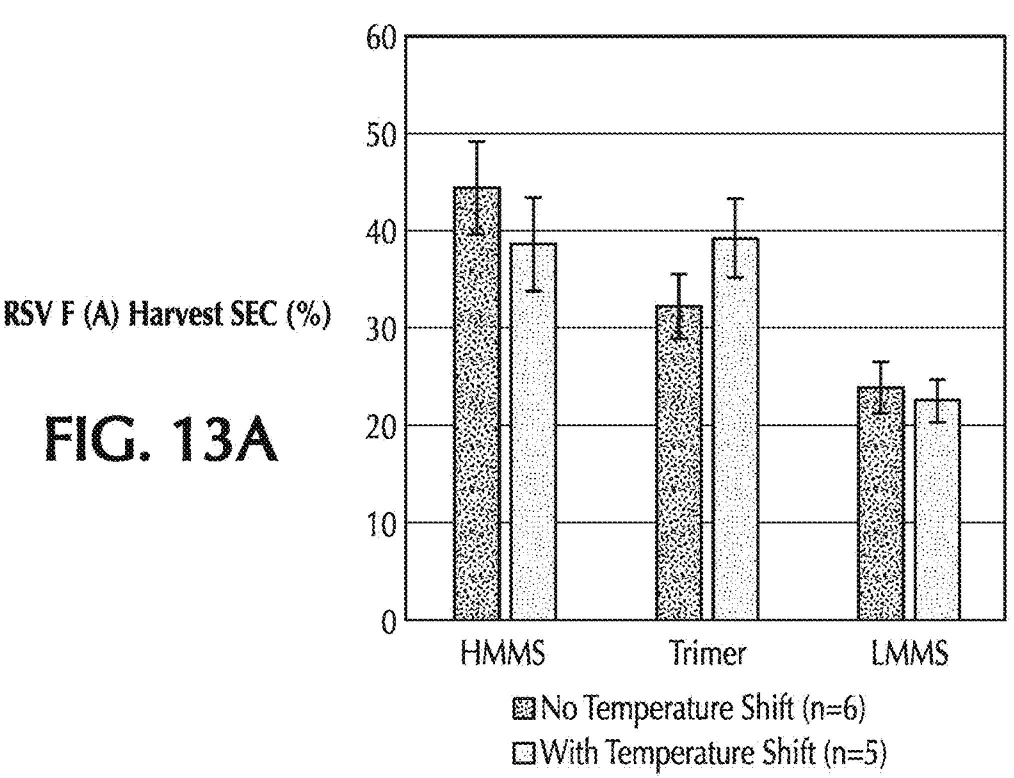
FIG. 13A shows the effect of the presence of a temperature shift on the percentage of HMMS, LMMS and RSV F protein of subtype A trimer as measured by size exclusion chromatography.
Figure 13B:
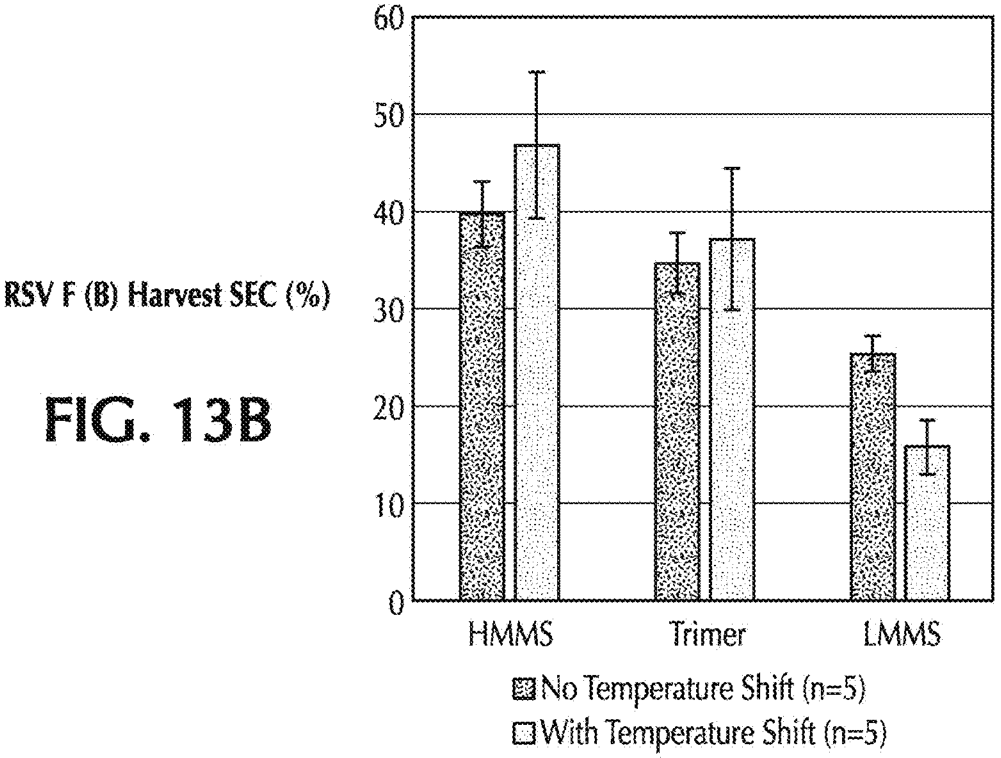
FIG. 13B shows the effect of the presence of a temperature shift on the percentage of HMMS, LMMS and RSV F protein of subtype B trimer as measured by size exclusion chromatography.
Figure 14A:
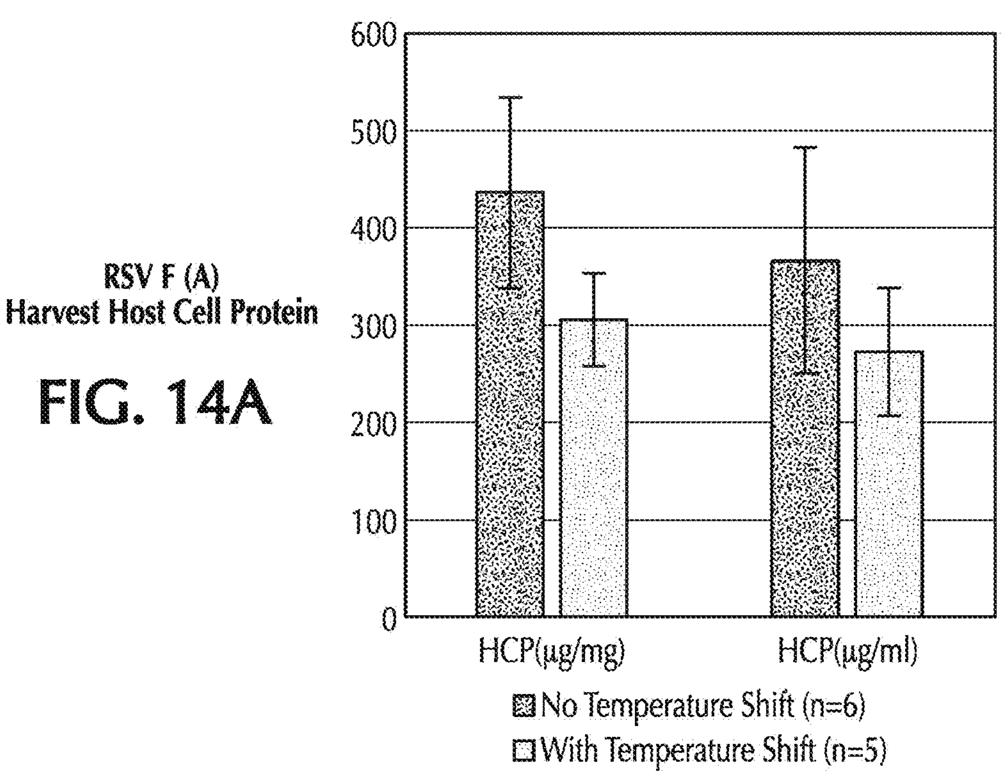
FIG. 14A shows the effect of the presence of a temperature shift on the titer of RSV F protein of subtype A as measured by RP-HPLC.
Figure 14B:
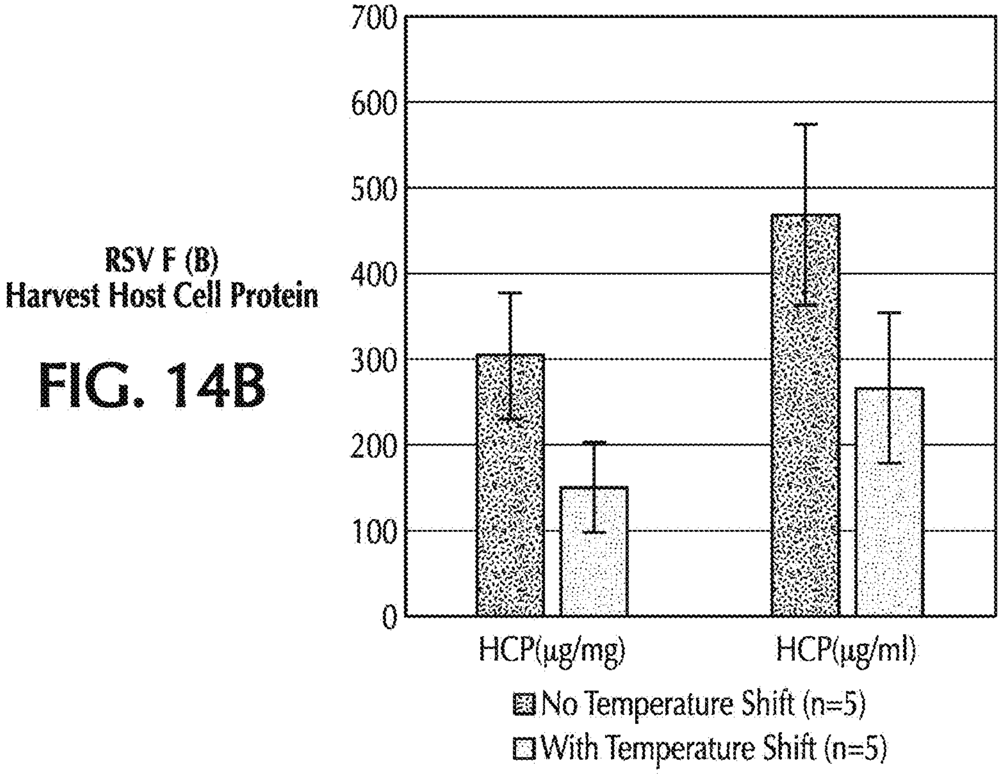
FIG. 14B shows the effect of the presence of a temperature shift on the titer of RSV F protein of subtype B as measured by RP-HPLC.
Figure 15A:
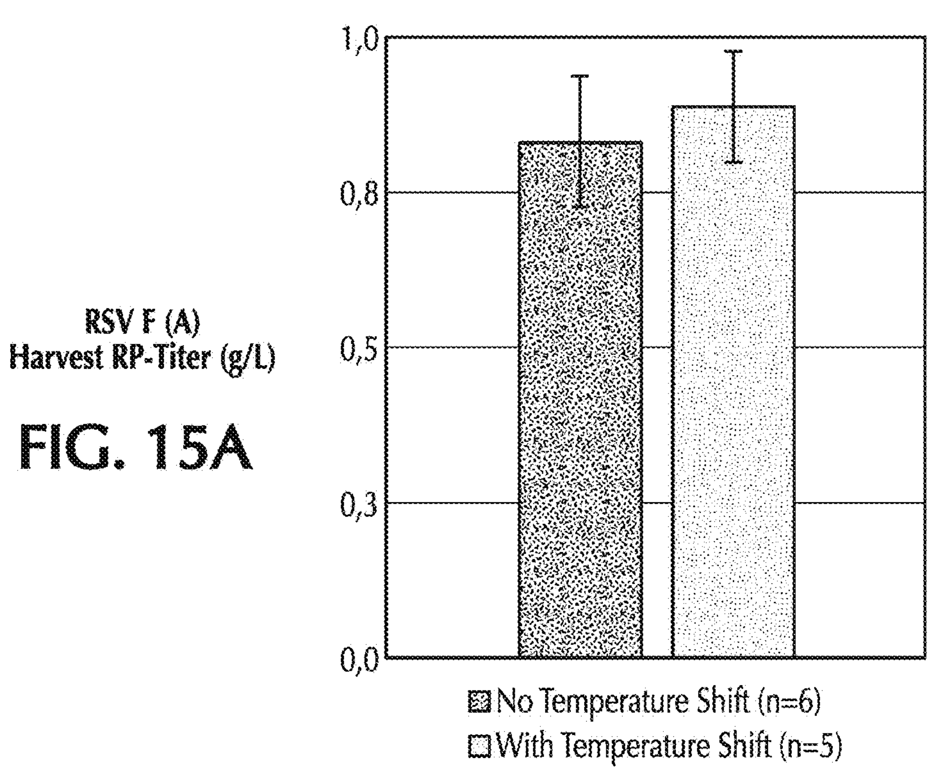
FIG. 15A shows the effect of the presence of a temperature shift on the amount of host cell protein (HCP) as measured by enzyme-linked immunoassay in material harvested from production of RSV F protein of subtype A.
Figure 15B:
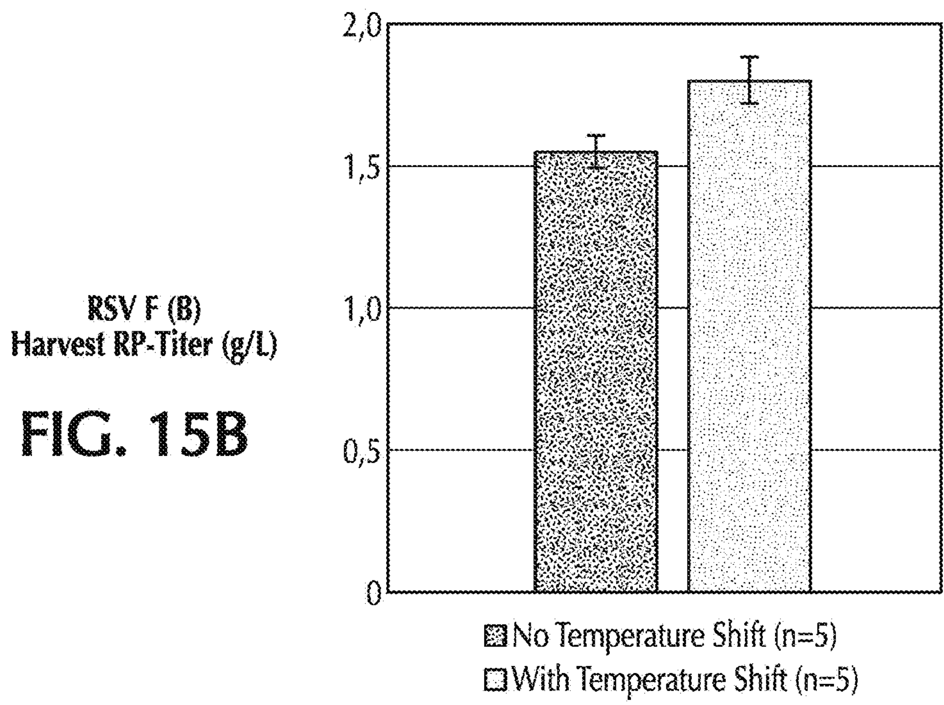
FIG. 15B shows the effect of the presence of a temperature shift on the amount of host cell protein (HCP) as measured by enzyme-linked immunoassay in material harvested from production of RSV F protein of subtype B.

The production temperature (post temperature shift) had a negative linear correlation with trimer and a positive linear correlation with LMMS, and HMMS for both antigens (see FIGS. 5A and 5B). The lowest HCP levels and the highest triter levels were obtained for the 31° C. production temperature (see FIGS. 7A, 7B and 8A and 8B).

1.3 Effect of Timing of Temperature Shift

In this experiment, the timing of the temperature shift was varied to assess its effect on titer, percentage of trimer, HMMS, LMMS triter, and the amount HCP. The results are shown in Table 4 and in FIGS. 9A, 9B, 10A, 10B, 11A, 11B, 12A and 12B.

TABLE 4

Effect of temperature shift timing

| Cell line | Growth Temp. (° C.) | Prod. Temp. (° C.) | Temp. Shift (hrs) | HCP (μg/mL) | RP-HPLC (g/L) | SEC HMMS (%) | SEC LMMS (%) | SEC Trimer (%) | Triter (g/L) |
|---|---|---|---|---|---|---|---|---|---|
| RSV F (A) | 34.5 | 31 | 114 | 273 | 0.61 | 46 | 28 | 26 | 0.16 |
| | 34.5 | 31 | 144 | 267 | 0.73 | 39 | 23 | 37 | 0.27 |
| | 34.5 | 31 | 185.5 | 375 | 0.44 | 42 | 29 | 28 | 0.12 |
| RSV F (B) | 34.5 | 31 | 114 | 167 | 1.79 | 37 | 17 | 46 | 0.83 |
| | 34.5 | 31 | 144 | 130 | 1.91 | 38 | 19 | 43 | 0.82 |
| | 34.5 | 31 | 185.5 | 194 | 1.82 | 33 | 18 | 49 | 0.90 |

A shift of the temperature at 144 hours after the start of the culture improved the amount of trimer, titer and level of HCP as compared to a shift at a different culture duration. This is true for both antigens and all attributes apart from trimer for RSV F (B) which was highest with a temperature shift at 185.5 hours after the start of the culture. The highest triter was obtained at a temperature shift of 144 hours for RSV F (A). Triter levels for RSV F (B) were similar at 144 and 114 hours, both lower than at 185.5 hours.

Example 2—Effect of Temperature Shift on RSV F Protein Production in CHO Cells This experiment was designed to assess the effect of the presence of a temperature shift on process performance, titer and trimer formation during the production of RSV F proteins of subtype A and B by CHO cells.

Production experiments were performed in 2 L Applikon® bioreactors with BioNet® controllers using conditions detailed in Table 5. All conditions were run in a fedbatch process comprising a phase where the amount of glucose provided to the cells is restricted (HipDOG from day 0 to day 5 for RSV F (A) and day 0 to day 4 for RSV F (B)) and using a cell culture medium without hydrocortisone.

TABLE 5

| Bioreactor Production Process Parameters | |
|---|---|
| Inoculation Density | $2.5 \times 10^6$ cells/mL |
| Process | Fed batch with HiPDOG |
| pH set point during HiPDOG | 7.025 +/− 0.025 |
| pH set point post HiPDOG | 7.05 +/− 0.15 |
| DO set point | 40% |
| Agitation | 80 W/m$^3$ |
| Impellers | Rushton (1) |
| Sparger | 100 μm sintered steel |
| Sparge | Pure $O_2$ |
| Headspace | Air/7% $CO_2$ mix @ 100 sccm |
| Feed Rate Post HiPDOG | 847A: 21 mL/L/day<br>847B: 25.5 mL/L/day |
| Glucose Feed | 500 g/L glucose, target 1.5 g/L |
| Titrant | 0.94M $Na_2CO_3$ + 0.06M $K_2CO_3$ |
| Antifoam | EX-CELL ® as needed |
| Process Duration | 12 days |
| Vessel Size | 2 L Applikon ® |
| Working Volume | 1 L |

Results are shown in Tables 6 and 7 and FIGS. 13A, 13B, 14A, 14B, 15A and 15C.

TABLE 6

Results with and without a temperature shift (averages).

| Average | Growth Temp. (° C.) | Prod. Temp (° C.) | Temp. Shift Day | RP-HPLC Titer (g/L) | HMMS (%) | Trimer (%) | LMMS (%) | HCP (μg/ml) | Triter (g/L) |
|---|---|---|---|---|---|---|---|---|---|
| RSV F (A) | 34.5 | 31 | 6 | 0.89 | 38 | 39 | 22 | 273 | 0.35 |
| | 34.5 | 34.5 | N/A | 0.86 | 45 | 32 | 23 | 381 | 0.27 |
| RSV F (A) | 34.5 | 31 | 6 | 1.81 | 47 | 37 | 16 | 267 | 0.67 |
| | 34.5 | 34.5 | N/A | 1.55 | 40 | 35 | 25 | 470 | 0.54 |

TABLE 7

Results with and without a temperature shift (standard deviations).
Standard Deviation

| Antigen | Growth Temp. (° C.) | Prod. Temp. (° C.) | Temp. Shift Day | RP-HPLC Titer (g/L) | HMMS (%) | Trimer (%) | LMMS (%) | HCP (μg/ml) | Triter (g/L) |
|---|---|---|---|---|---|---|---|---|---|
| RSV F (A) | 34.5 | 31 | 6 | 0.09 | 5 | 4 | 2 | 65 | 0.05 |
| | 34.5 | 34.5 | N/A | 0.07 | 5 | 4 | 2 | 124 | 0.03 |
| RSV F (A) | 34.5 | 31 | 6 | 0.08 | 7 | 7 | 3 | 88 | 0.13 |
| | 34.5 | 34.5 | N/A | 0.06 | 3 | 3 | 2 | 105 | 0.06 |

The presence of a temperature shift increased trimer levels, decreased HOP, and increased titer for both antigens (see FIGS. 13A, 13B, 14A, 14B, 15A, and 15B).

Example 3—Effect of Glucocorticoid Compounds on RSV F Protein Production in CHO Cells This experiment was designed to understand the effect of glucocorticoid compounds such as hydrocortisone on titer and product quality of RSV F protein of subtype A and B produced in CHO cells.

Production experiments were performed in 2 L Applikon® bioreactors with BioNet® controllers using the process detailed in Table 8 in cell culture media with or without hydrocortisone.

All bioreactors were run at 34.5° C. and a temperature shift to 31° C. was performed with bioreactor (08) on day 6. Glucose was provided in a restricted manner (Hipdog) from day 0 to day 4 for RSV F (B) and day 0 to day 5 for RSV F (A).

TABLE 8

| Bioreactor Production Process Parameters | |
|---|---|
| Inoculation Density | $2.5 \times 10^6$ cells/mL |
| Process | Fed batch with HiPDOG |
| HiPDOG End | Day 4 for RSV F (B); Day 5 for RSV F (A) |
| pH set point during HiPDOG | 7.025 +/− 0.025 |
| pH set point post HiPDOG | 7.05 +/− 0.15 |
| DO set point | 40% |
| Temperature | 34.5° C. |
| Agitation | 80 W/m$^3$ |
| Impellers | Rushton (1) |
| Sparger | 100 μm sintered steel |
| Sparge | Pure $O_2$ |
| Headspace | Air/7% $CO_2$ mix @ 100 sccm |
| Production Medium | +/−0.54 mg/L hydrocortisone |
| Feed Medium | +/−1.08 mg/L hydrocortisone |
| Feed Rate Post HiPDOG | RSV F (A): 21 mL/L/day<br>RSV F (B): 25.5 mL/L/day |
| Glucose Feed | 500 g/L glucose with 7.5 g/L cysteine, target 1.5 g/L |
| Titrant | 0.94M sodium carbonate + 0.06M potassium carbonate |
| Antifoam | EX-CELL ® as needed |
| Process Duration | 12 days |
| Vessel Size | 2 L Applikon |
| Working Volume | 1 L |

Figure 16:
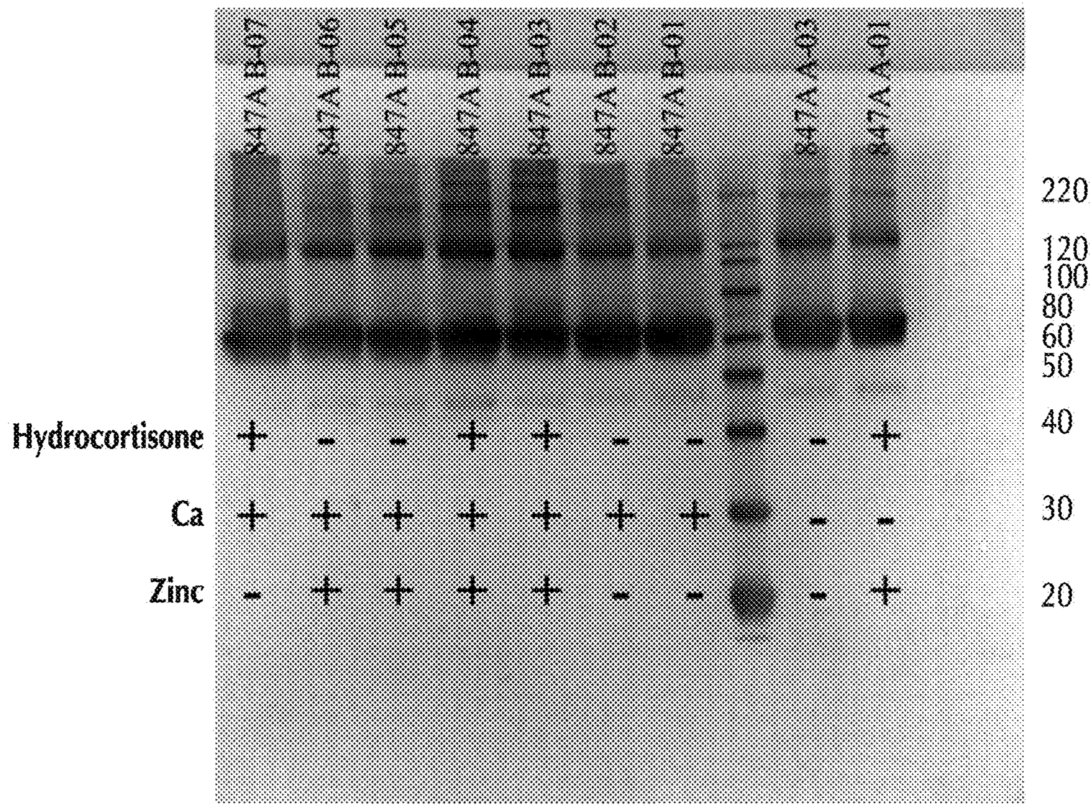
FIG. 16 shows a western blot of the material harvested from production run from 9 bioreactors with various culture conditions after a hydrophobic interaction chromatography (HIC) on material harvested from production of RSV F protein of subtype A.
Figure 17:
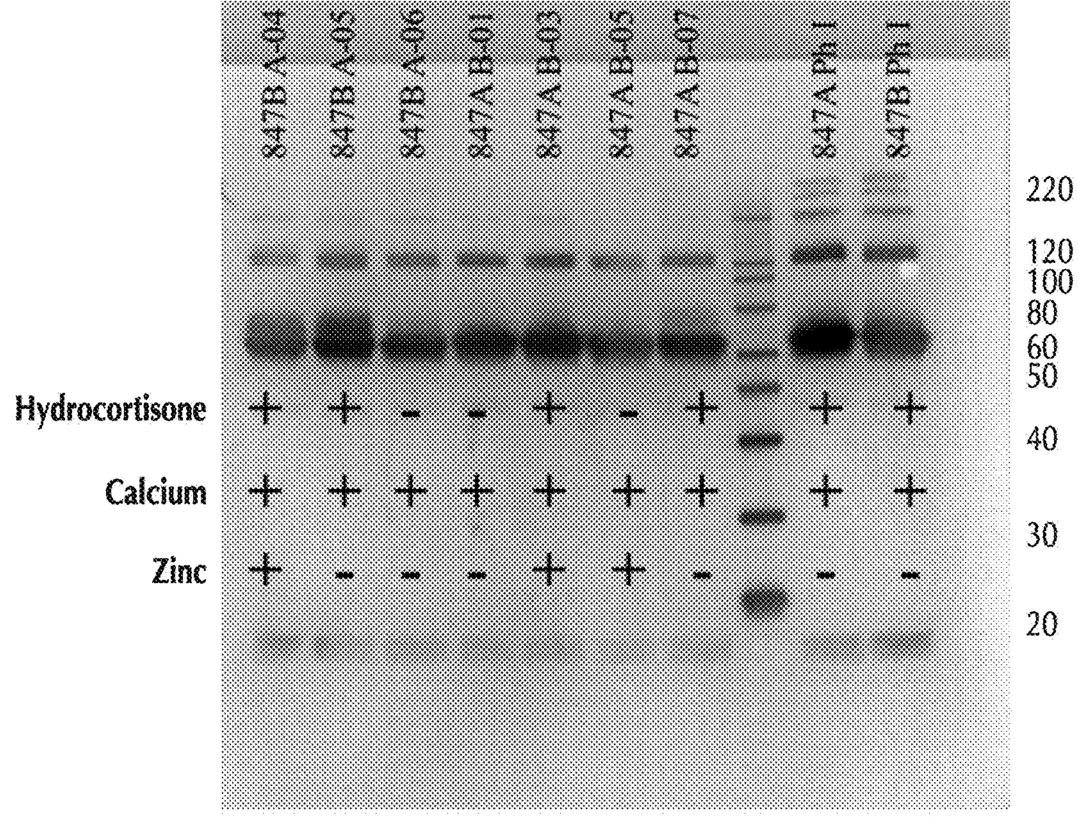
FIG. 17 shows a western blot of the material harvested from production run from 9 bioreactors with various culture conditions after a hydrophobic interaction chromatography (HIC) on material harvested from production of RSV F protein of subtype B.

Hydrocortisone had a negative effect on furin processing of RSV F protein as indicated by the Western blot results shown in FIGS. 16 and 17. The Western blot allows monitoring of processed RSV F (A) or RSV F (B) monomers and related species. Pre-fusion F trimers are specifically recognized by mAb AM14 (Gilman M S et al, PLoS Pathogens, 11(7), 2015). The term "AM14" refers to an antibody described in WO 2008/147196 A2, which has a heavy chain variable domain comprising an amino acid sequence of SEQ ID NO:3 and a light chain variable domain comprising an amino acid sequence of SEQ ID NO:4. Results are collected to monitor the process capabilities and levels of processed RSV F (A) or RSV F (B) monomer, partially processed or unprocessed F+p27 or other size variants. The lanes for those conditions which contained hydrocortisone (B-07, B-04, B-03 and A-01 in FIG. 16 and A-04, A-05, B-03, B-07) present a smear directly above the RSV band (approximately 60 kDa) as identified by binding of the AM-14 antibody. The presence of a smear is an indication of partially processed RSV variants.

Therefore, it is advantageous not to include hydrocortisone or other related glucocorticoid compound in the cell culture medium to be used in the method of the invention in order to improve the amount of processed material suitable for being used in vaccine composition in particular in the form of trimer.

Example 4—Effect of HiPOG on RSV F Production in CHO Cells

Stabilization of the prefusion conformation is important for the RSV protein as the postfusion conformation is energetically favored and less immunogenic, with the transition from prefusion to postfusion being irreversible. RSV F protein of subtype A and B can be engineered to stabilize the protein in the prefusion conformation and disulfide bonds contribute to this stability. Consequentially, disulfide bond integrity could impact the stability of the desired conformation. An inter-subunit disulfide bond in RSV was found to be unpaired to a small extent in the initial fed batch process. The two corresponding unpaired cysteines were found modified with cysteinyl moieties. This modification is measured and reported as "cysteinylation" which is measured by amino acid analysis coupled to a QDa mass detector.

This experiment was designed to understand the effect of HiPOG on the level of cysteinylation on the RSV F of subtype A and B produced in CHO cells. Bioreactor parameters are listed in Table 9.

TABLE 9

| Bioreactor Production Process Parameters | |
|---|---|
| Inoculation Density | $3.0 \times 10^6$ cells/mL |
| Process | Fed batch with or without HiPDOG |
| HiPDOG End | Day 4 for RSV F (B); Day 5 for RSV F (A) |
| pH set point during HiPDOG | 7.075 +/− 0.025 |
| pH set point post HiPDOG | 7.05 +/− 0.15 |
| DO set point | 40% |
| Temperature | 34.5° C. throughout |
| Agitation | 80 W/m$^3$ |
| Impellers | Rushton (1) |
| Sparger | 100 μm sintered steel |
| Sparge | Pure $O_2$ |
| Headspace | Air/7% $CO_2$ mix @ 100 sccm |
| Feed Rate Post HiPDOG | RSV F subtype A: 21 mL/L/day<br>RSV F subtype B: 25.5 mL/L/day |
| Glucose Feed | 500 g/L glucose, target 2 g/L |
| Titrant | 0.94M sodium carbonate + 0.06M potassium carbonate |
| Antifoam | EX-CELL ® as needed |
| Process Duration | 12 days |
| Vessel Size | 2 L Applikon |
| Working Volume | 1 L |

The level of cysteinylation was reduced for both the RSV F (A) and RSV F (B) antigens when HiPDOG control was employed (Table 10).

TABLE 10

| Cysteinylation Results | | |
|---|---|---|
| Cell line | Condition | Cysteinylation (%) |
| RSV F (A) | Without HiPDOG | 7.63 |
| RSV F (A) | With HiPDOG | 3.84 |

TABLE 10-continued

| Cysteinylation Results | | |
|---|---|---|
| Cell line | Condition | Cysteinylation (%) |
| RSV F (B) | Without HiPDOG | 2.08 |
| RSV F (B) | With HiPDOG | 1.38 |

In addition, titer was improved for both the RSV F (A) and RSV F (B) antigens when HiPDOG was employed (Table 11). The titer measurements reported are after the first purification step (ultrafiltration).

TABLE 11

| Titer Results | | |
|---|---|---|
| Cell line | Condition | Ultrafiltration Pool Titer (g/L) |
| RSV F (A) | Without HiPDOG | 0.70 |
| RSV F (A) | With HiPDOG | 1.80 |
| RSV F (B) | Without HiPDOG | 1.87 |
| RSV F (B) | With HiPDOG | 3.43 |

Example 5—Large Scale Manufacturing Process

The suitability of the method of the invention for use at large scale was tested. CHO cells expressing RSV protein F of subtype A or subtype B were cultured in a 12 day fed batch process using HiPDOG, a growth temperature of 34.5° C. and a production temperature of 31° C. with a temperature shift on day 6. As shown in below Table 12, the method of the invention provided advantageous triter values even when performed in 2500 or 12500 L bioreactors.

TABLE 12

| Results from large scale experiments | | | | | | | |
|---|---|---|---|---|---|---|---|
| Cell line | Scale (L) | HCP (ug/mL) | RP-HPLC (g/L) | HMMS (%) | Trimer (%) | LMMS (%) | Triter (g/L) |
| RSV F (A) | 2500 | 303 | 0.86 | 38 | 38 | 24 | 0.33 |
| | 12500 | 300 | 0.84 | 39 | 36 | 24 | 0.30 |
| RSV F (B) | 2500 | 268 | 1.49 | 40 | 41 | 19 | 0.61 |
| | 12500 | 211 | 1.79 | 39 | 38 | 23 | 0.68 |

Listing of Raw Sequences

SEQ ID NO: 1. Amino Acid Sequence of the Full Length F0 of Native RSV A2 (GenBank GI: 138251; Swiss Prot P03420)
MELLILKANAITTILTAVTFCFASGQNITEEFYQSTCSAVSKGYLSALRTGWYTSVITIE
LSNIKENKCNGTDAKVKLIKQELDKYKNAVTELQLLMQSTPPTNNRARRELPRFMNYTLNNAKKTNVTLSKKRKRRF
LGFLLGVGSAIASGVAVSKVLHLEGEVNKIKSALLSTNKAVVSLSNGVSVLTSKVLDLKNYIDKQLLPIVNKQSCSISNIE
TVIEFQQKNNRLLEITREFSVNAGVTTPVSTYMLTNSELLSLINDMPITNDQKKLMSNNVQIVRQQSYSIMSIIKEEVL
AYVVQLPLYGVIDTPCWKLHTSPLCTTNTKEGSNICLTRTDRGWYCDNAGSVSFFPQAETCKVQSNRVFCDTMNSL
TLPSEINLCNVDIFNPKYDCKIMTSKTDVSSSVITSLGAIVSCYGKTKCTASNKNRGIIKTFSNGCDYVSNKGMDTVSV
GNTLYYVNKQEGKSLYVKGEPIINFYDPLVFPSDEFDASISQVNEKINQSLAFIRKSDELLHNVNAGKSTTNIMITTIIIVI
IVILLS LIAVGLLLYCKARSTPVTLSKDQLSGINNIAFSN SEQ ID NO: 2. Amino Acid Sequence of the Full Length F0 of Native RSV B (18537 strain; GenBank GI: 138250; Swiss Prot P13843)
MELLIHRSSAIFLTLAVNALYLTSSQNITEEFYQSTCSAVSRGYFSALRTGWYTSVITIE
LSNIKETKCNGTDTKVKLIKQELDKYKNAVTELQLLMQNTPAANNRARREAPQYMNYTINTTKNLNVSISKKRKRRF
LGFLLGVGSAIASGIAVSKVLHLEGEVNKIKNALLSTNKAVVSLSNGVSVLTSKVLDLKNYINNRLLPIVNQQSCRISNIE
TVIEFQQMNSRLLEITREFSVN
AGVTTPLSTYMLTNSELLSLINDMPITNDQKKLMSSNVQIVRQQSYSIMSIIKEEVLAYV
VQLPIYGVIDTPCWKLHTSPLCTTNIKEGSNICLTRTDRGWYCDNAGSVSFFPQADTCKVQSNRVFCDTMNSLTLPS
EVSLCNTDIFNSKYDCKIMTSKTDISSSVITSLGAIVSCYGKTKCTASNKNRGIIKTFSNGCDYVSNKGVDTVSVGNTLY
YVNKLEGKNLYVKGEPIINYYDPLVFPSDEFDASISQVNEKINQSLAFIRRSDELLHNVNTGKSTTNIMITTIIIVIIVVLLS
LIAIGLLLYCKAKNTPVTLSKDQLSGINNIAFSK SEQ ID NO: 3: Amino Acid Sequence of Heavy Chain Variable Domain of Antibody AM14:
EVQLVESGGGVVQPGRSLRLSCAASGFSFSHYAMHWVRQAPGKGLEWVAVISYDGENTYYADSVKGRFSISRDNS
KNTVSLQMNSLRPEDTALYYCARDRIVDDYYYYGMDVWGQGATVTVSS SEQ ID NO: 4: Amino Acid Sequence of Light Chain Variable Domain of Antibody AM14:
DIQMTQSPSSLSASVGDRVTITCQASQDIKKYLNWYHQKPGKVPELLMHDASNLETGVPSRFSGRGSGTDFTLTISS
LQPEDIGTYYCQQYDNLPPLTFGGGTKVEIKRTV

The invention claimed is:

1. A method for producing an RSV F protein trimer, comprising the steps of:

(i) culturing mammalian cells that contain a gene encoding an RSV F protein in a cell culture medium, wherein said culturing comprises a growth phase and a production phase, and (ii) providing, during the growth phase and/or the production phase, glucose in a restricted manner to the cell culture by feeding glucose to the cell culture in response to rise of pH above a predetermined pH value in excess of a pH set point, wherein feeding glucose to the cell culture continues until the pH decreases to reach the pH set point of the culture, wherein the RSV F protein comprises an engineered disulfide mutation.

2. The method according to claim 1, wherein said growth phase is carried out at a temperature between about 33° C. and 35° C.

3. The method according to claim 1, wherein the temperature is shifted to a lower temperature at the beginning of said production phase.

4. The method according to claim 3, wherein said production phase begins between day 3 and day 7 of the culture.

5. The method according to claim 1, wherein the predetermined pH value corresponds to an increase of 0.01 to 0.10 above the pH set point of the culture.

6. The method according to claim 5, wherein the pH set point of the cell culture is between pH 6.70 and pH 7.30.

7. The method according to claim 6, wherein the pH set point of the cell culture is between pH 6.90 and pH 7.20.

8. The method according to claim 1 wherein the mammalian cells are selected from BALB/c mouse myeloma line, human retinoblasts (PER.C6), monkey kidney cells, human embryonic kidney line (293), baby hamster kidney cells (BHK), Chinese hamster ovary cells (CHO), mouse sertoli cells, African green monkey kidney cells (VERO-76), human cervical carcinoma cells (HeLa), canine kidney cells, buffalo rat liver cells, human lung cells, human liver cells, mouse mammary tumor cells, TRI cells, MRC 5 cells, FS4 cells, or human hepatoma line (Hep G2).

9. The method according to claim 1 wherein the mammalian cells are Chinese hamster ovary cells (CHO).

10. The method according to claim 1, wherein the RSV F protein is of subtype A.

11. The method according to claim 1, wherein the RSV F protein is of subtype B.

12. The method according to claim 1, wherein said engineered disulfide mutation stabilizes the trimer in the pre-fusion conformation.

13. The method according to claim 1 wherein the RSV F protein comprises a combination of engineered disulfide mutations selected from the group consisting of:

A149C and Y458C; A153C and K461C; A329C and S430C; A424C and V450C; A74C and E218C; D338C and K394C; D401C and Y417C; D486C and D489C; D486C and E487C; E30C and L410C; E30C and S466C; E60C and D194C; E60C and K196C; E92C and N254C; F137C and T337C; G139C and P353C; G139C and Q354C; G143C and S404S; G145C and M370C; G151C and I288C; G151C and N302C; G151C and Q302C; G151C and V300C; I148C and Y286C; I288C and V300C; I28C and G464C; 157C and S190C; I59C and L193C; I59C and L297C; I59C and V192C; K176C and S190C; K399C and Q494C; K399C and S485C; K427C and D448C; K508C and S509C; K77C and I217C; L138C and P353C; L138C and T337C; L142C and N371C; L158C and 1291C; L158C and S290C; L171C and K191C; L193C and I59C; L297C and I292C; L321C and L334C; L381C and N388C; L381C and Y391C; L410C and G464C; L410C and S466C; L48C and V308C; L61C and L195C; N183C and K423C; N183C and N428C; N331C and D401C; N515C and V516C; N88C and N254C; P320C and S415C; P320C and T335C; Q34C and G471C; Q98C and Q361C; R106C and V144C; S145C and 460C; S146C and I407C; S146C and N460C; S155C and I288C; S155C and S290C; S155C and V300C; S238C and E92C; S238C and Q279C; S319C and I413C; S319C and S415C; S346C and N454C; S35C and G471C; S403C and T420C; S403C and Y417C; S443C and S466C; S46C and T311C; S55C and L188C; S62C and D200C; S62C and I199C; S62C and K196C; T103C and A147C; T103C and I148C; T189C and A177C; T189C and V56C; T357C and N371C; T369C and T455C; T374C and N454C; T397C and E487C; T397C and P484C; T400C and D489C; T522C and T523C; T54C and G151C; T54C and V154C; T58C and K191C; V144C and V406C; V154C and V300C; V164C and E294C; V164C and K293C; V402C and L141C; V406C and I413C; V56C and T189C; V56C and V187C; W341C and F352C; W52C and S150C; Y33C and V469C; A329C and S430C with insertion of CAA between positions 329 and 330; N183C and K423C with insertion of AAA between positions 182 and 183; N183C and N427G with insertion of C between positions 427 and 428; N183C and N428C with insertion of G between positions 182 and 183; N345C and N454G with insertion of C between positions 453 and 454; S145C and 460C with insertion of AA between positions 146 and 147; S146C and N460C with insertion of G between position 460 and 461; S238G and Q279C with insertion of C between positions 238 and 239; S493C with insertion of C between positions 329 and 330; and T374C and N454G with insertion of C between positions 453 and 454.

14. The method according to claim 2, wherein said growth phase is carried out at a temperature between about 34° C. and 35° C.

15. The method according to claim 1, wherein the duration of said growth phase is between about 4 days and 10 days.

16. The method according to claim 15, wherein the duration of said growth phase is about 6 days.

17. The method according to claim 3, wherein said production phase is carried out at a temperature between about 30° C. and 32° C.

18. The method according to claim 17, wherein said production phase is carried out at a temperature of about 31° C.

19. The method according to claim 3, wherein the duration of said production phase is between about 4 days and 8 days.

20. The method according to claim 19, wherein the duration of said production phase is about 6 days.

21. The method according to claim 7, wherein the pH set point of the cell culture is between about pH 7.0 and pH 7.1.

22. The method according to claim 1, wherein glucose is provided in restricted manner for about 1 to 6 days during the growth phase.

23. The method according to claim 1, wherein glucose is provided in restricted manner starting on day 0 to day 2 of the culture.

24. The method according to claim 1, wherein said method is effective to reduce the level of cysteinylation of said RSV F protein as compared to the level of cysteinylation of RSV F protein produced in an otherwise similar method in which glucose is not provided in a restricted manner.

25. The method according to claim 1, wherein said culturing is carried out in fed batch culture.

* * * * *

SEQUENCE LISTING

<160> NUMBER OF SEQ ID NOS: 4

<210> SEQ ID NO 1
<211> LENGTH: 574
<212> TYPE: PRT
<213> ORGANISM: Human respiratory syncytial virus

<400> SEQUENCE: 1

Met Glu Leu Leu Ile Leu Lys Ala Asn Ala Ile Thr Thr Ile Leu Thr
1 5 10 15

-continued

```
Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430
```

```
Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 2
<211> LENGTH: 574
<212> TYPE: PRT
<213> ORGANISM: Human respiratory syncytial virus

<400> SEQUENCE: 2

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Arg Leu Leu Pro Ile Val Asn
        195                 200                 205

Gln Gln Ser Cys Arg Ile Ser Asn Ile Glu Thr Val Ile Glu Phe Gln
    210                 215                 220

Gln Met Asn Ser Arg Leu Leu Glu Ile Thr Arg Glu Phe Ser Val Asn
225                 230                 235                 240
```

```
Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```

<210> SEQ ID NO 3
<211> LENGTH: 123
<212> TYPE: PRT
<213> ORGANISM: Artificial Sequence
<220> FEATURE:
<223> OTHER INFORMATION: Synthetic peptide sequence

<400> SEQUENCE: 3

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser His Tyr
            20                  25                  30
```

-continued

```
Ala Met His Trp Val Arg Gln Ala Pro Gly Lys Gly Leu Glu Trp Val
        35                  40                  45

Ala Val Ile Ser Tyr Asp Gly Glu Asn Thr Tyr Tyr Ala Asp Ser Val
    50                  55                  60

Lys Gly Arg Phe Ser Ile Ser Arg Asp Asn Ser Lys Asn Thr Val Ser
65                  70                  75                  80

Leu Gln Met Asn Ser Leu Arg Pro Glu Asp Thr Ala Leu Tyr Tyr Cys
                85                  90                  95

Ala Arg Asp Arg Ile Val Asp Asp Tyr Tyr Tyr Tyr Gly Met Asp Val
            100                 105                 110

Trp Gly Gln Gly Ala Thr Val Thr Val Ser Ser
        115                 120


<210> SEQ ID NO 4
<211> LENGTH: 111
<212> TYPE: PRT
<213> ORGANISM: Artificial Sequence
<220> FEATURE:
<223> OTHER INFORMATION: Synthetic peptide sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Lys Lys Tyr
            20                  25                  30

Leu Asn Trp Tyr His Gln Lys Pro Gly Lys Val Pro Glu Leu Leu Met
        35                  40                  45

His Asp Ala Ser Asn Leu Glu Thr Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Ile Gly Thr Tyr Tyr Cys Gln Gln Tyr Asp Asn Leu Pro Pro
                85                  90                  95

Leu Thr Phe Gly Gly Gly Thr Lys Val Glu Ile Lys Arg Thr Val
            100                 105                 110
```